United States Patent
Rheinstädter et al.

(10) Patent No.: US 11,771,650 B2
(45) Date of Patent: Oct. 3, 2023

(54) HYBRID BIOLOGICAL MEMBRANES, METHODS OF MAKING AND USES THEREOF

(71) Applicant: McMaster University, Hamilton (CA)

(72) Inventors: Maikel C. Rheinstädter, Hamilton (CA); Sebastian Himbert, Hamilton (CA); Matthew Blacker, Toronto (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 17/127,472

(22) Filed: Dec. 18, 2020

(65) Prior Publication Data

US 2021/0205218 A1    Jul. 8, 2021

Related U.S. Application Data

(60) Provisional application No. 62/951,586, filed on Dec. 20, 2019.

(51) Int. Cl.
*A61K 9/127*    (2006.01)
*A61K 35/18*    (2015.01)

(52) U.S. Cl.
CPC .......... *A61K 9/1271* (2013.01); *A61K 9/1277* (2013.01); *A61K 35/18* (2013.01)

(58) Field of Classification Search
None
See application file for complete search history.

(56) References Cited

U.S. PATENT DOCUMENTS

2016/0228839 A1 *   8/2016   Cho  .................  G01N 33/54393

FOREIGN PATENT DOCUMENTS

WO    WO-2019022671 A1 *   1/2019   .......... A61K 9/1075

OTHER PUBLICATIONS

Robert Deak, Judith Mihály, Imola Cs. Szigyártó, András Wacha, Gábor Lelkes,Attila Bóta. "Physicochemical characterization of artificial nanoerythrosomesderived from erythrocyte ghost membranes." Colloids and Surfaces B, vol. 135, 2015, pp. 225-234 and 5 pages of supplementary info. (Year: 2015).*
Yuko T. Sato et al. "Engineering hybrid exosomes by membrane fusion with liposomes." Scientific Reports, 6:21933 | DOI: 10.1038/srep21933, 2016, pp. 1-11. (Year: 2016).*
Antonio P. Costa, Xiaoming Xu, and Diane J. Burgess. "Freeze-Anneal-Thaw Cycling of Unilamellar Liposomes: Effect on Encapsulation Efficiency." Pharmaceutical Research, vol. 31, 2014, pp. 97-103. (Year: 2014).*
Sebastian Himbert. "The Molecular Structure of Human Red Blood Cell Membranes from Highly Oriented, Solid Supported Multi-Lamellar Membranes." Scientific Reports, 7:39661 | DOI: 10.1038/srep39661, 2017, pp. 1-14. (Year: 2017).*
Elena V. Batrakova, Myung Soo Kim. "Using exosomes, naturally-equipped nanocarriers, for drug delivery." Journal of Controlled Release 219 (2015), pp. 396-405. (Year: 2015).*

(Continued)

*Primary Examiner* — Isaac Shomer
(74) *Attorney, Agent, or Firm* — Denise L. Mayfield; DYKEMA GOSSETT PLLC

(57) ABSTRACT

Described herein is a hybrid biological membrane comprising an endogenous bilayer doped with one or more synthetic lipid molecules. Also described herein is a method of preparing a hybrid biological membrane, the method comprising doping an endogenous bilayer with one or more synthetic lipid molecules.

6 Claims, 11 Drawing Sheets

(56) References Cited

OTHER PUBLICATIONS

Krivic, et al . . . , "Erythro-PmBs: A Selective Polymyxin B Delivery System Using Anti-body-COnjugated Hybrid Erythrocyte Lliposomes," ACS Infect. Dis. 2022, 8, 2059-2072.
Khondker, et al., "Carbapenems and Lipid Bilayers: Localization, Partitioning, and Energetics," ACS infectious diseases, 2018, 4, 926.
Samad, et al., Liposomal Drug Delivery Systems: An Update Review,: Current drug delivery, 2007, 4, 297.
Pattni, et al., "New Development in Liposomal Drug Delivery," Chemical reviews, 2015, 115, 10938.
Sercombe, et al., "Advances and Challenges of Liposome Assisted Drug Delivery," Frontiers in pharmacology, 2015, 6, 286.
Ihler, et al., "Enzyme Loading of Erthrocytes," Proceedings of the National Academy of Sciences, 1973, 70, 2663.
Muzykantov, "Drug delivery by red blood cells: vascular carriers designed by Mother Nature," Expert opinion on drug delivery, 2010, 7, 403.
Magnani, "Engineered red blood cells as therapeutic agents," American journal of hematology, 2017, 92, 979.
Leuzzi, et al., "Positive effect of erythrocyte-delivered dexamethasone in ataxzia-telegiectasia," Neurology-Neuroimmunology Neuroinammation, 2015, 2, e98.
Zaitsev, et al., "Sustained thromboprophylais mediated by an RGBC-targeted pro-urokinase zymogen activiated at the site of clot formation," Blood, 2010, 115, 5241.
Zaitsev, et al., "Targeting recombinant thrombomodulin fusion protein to red blood cells provides multifaceted thromboprophylaxis," Blood, 2012, 119, 4779.
Krivic, et al . . . , "Erythro-PmBs: A Selective Polymyxin B Delivery System Using Anti-body-Conjugated Hybrid Erythrocyte Liposomes," ACS Infectious Diseases 2022, 8, 2059-2072.
Armstead, et al., "RBC-coupled tPA Prevents Impairment of Cerebral Vasodilatory Responses and Tissue Injury in Pediatric Cerebral Hypoxia/Ischemia Through Inhibition of ERK MAPK Activation," Journal of Cerebral Blood Flow & Metabolism, 2009, 29, 1463.
Armstead, et al., "Signaling, Delivery and Age as Emerging Issues in the Benefit/Risk Ratio Outcome of tPA for Treatment of CNS Ischemic Disorders," Journal of Neurochemistry, 2010, 113, 303.
Lorentz, et al., "Engineering binding to erythrocytes induces immunological tolerance to E. coli Asparaginase," Science Advances, 2015, 1, e1500112.
Pan, et al.,"The Effect of Polymeric Nanoparticles on Biocompatibility of Carrier Red Blood Cells," PLOS One, 2016, 11, e0152074.
Muzykantov, et al., "Regulation of the Complement-Mediated Elimination of Red Blood Cells Modified with Biotin and Streptavidin," Analytical Biochemistry, 1996, 241, 109.
He, et al., "Erythroliposomes: Integrated Hybrid Nanovesicles Composed of Erythrocyte Membranes and Artificial Lipid Membranes for Pore-Forming Toxin Clearance," ACS Nano, 2019, 13, 4148.
Qi, et al., "CHARMM-GUI Martini Maker for Coarse-Grained Simulations with the Martini Force Field," Journal of Chemical Theory and Computation, 2015, 11, 4486.
Jo, et al., "Software News and Updates—CHARMM-GUI: A Web-Based Graphical User Interface for CHARMM," Journal of Computational Chemistry, 2008, 29, 1859.
Wiener, et al., "Structure of the fully hydrated gel phase of dipalmitoylphosphatidylcholine," Biophys. J., 1989, 55, 309.
Morales-Penningston, et al., "GUV Preparation and Imaging: Minimizing artifacts," Biochimica et Biophysica Acta (BBA)-Biomembranes, 2010, 1798, 1324.
Skaug, "The Impact of Texas Red on Lipid Bilayer Properties," The Journal of Physical Chemistry B, 2011, 115, 8500.
Juhasz, et al., "Quantitative characterization of coexisting phases in DOPC/DPPC/Cholesterol mixtures: Comparing confocal fluorescence microscopy and deuterium nuclear magnetic resonance," Biochimica et Biophysica Acta (BBA)-Biomembranes, 2009, 1788, 2541.
Juhasz, et al., "Fluorescent probe partitioning in giant unilamellar vesicles of 'lipid raft' mixtures," Biochemical Journal, 2010, 430, 415.
Juhasz, et al., "Fluorescent probe partitioning in GUVs of binary phospholipid mixtures: Implications for interpreting phase behavior," Biochimica et Biophysica Acta 1818 (2012) 19-26.
Veatch, et al., "Seeing spots: Complex phase behavior in simple membrantes," Biochimica et Biophysica Acta (BBA)-Molecular Cell Research, 2005, 1746, 172.
Villa, et al., "Biocompatible coupling of therapeutic fusion proteins to human erythrocytes," Blood Advances, 2018, 2, 165.
Muzykantov, et al., "Avidin-induced lysis of biotinylated erythrocytes by homologous complement via the alternative pathway depends on avidin's ability of multipoint binding with biotinylated membrane,"Journal of Immunological Methods, 1993, 158, 183.
Muzykantov, et al., "Avidin attachment to biotinylated amino groups of the erythrocyte membrane eliminates homologous restriction of both classical and alternative pathways of the complement," Biochimica et Biophysica Acta (BBA)-Biomembranes, 1992, 1107, 119.
Zaltzman, et al., "Enhanced complement susceptibility of avidin-biotin-treated human erythrocytes is a consequence of neutralization of the complement regulators CD59 and decay accelerating factor," Biochemical Journal, 1995, 307, 651.
Nii, et al., "Encapsulation efficiency of water-soluble and insoluble drugs in liposomes prepared by the microencapsulation vesicle method," International Journal of Pharmaceutics, 2005, 298, 198.
Riberio, et al., "Translocating the blood-brain barrier using electrostatics," Frontiers in Cellular Neuroscience, 2012, 6, 44.
Bhattacharjee, "DLS and zeta potential—What they are and what they are not?" Journal of Controlled Release, 2016, 235, 337.
Lew, et al., "Mechanism of Spontaneous Inside-Out Vesiculation of Red Cell Mem branes,"The Journal of Cell Biology, 1988, 106, 1893.
Dodge, et al., "Composition of phospholipids and of phospholipid fatty acids and aldehydes in human red cells," Journal of Lipid Research, 1967, 8, 667.
Toppozini, et al., "The Structure of Cholesterol in Lipid Rafts," Physical Review Letters, 2014, 113, 228101.
Armstrong, et al., "The Observation of Highly Ordered Domains in Membranes with Cholesterol," PLOS One, 2013, 8, e66162.
Rheinstädter, et al., "Small-scale structure in fluid cholesterol-lipid biyayers," Current Opinion in Colloid & Interface Science, 2013, 18, 440.
Lingwood, et al., "Lipid Rafts as a Membrane-Organizing Principle," Science, 2010, 327, 46.
Ingolfsson, et al., "Lipid Organization of the Plasma Membrane," Journal of the American Chemical Society, 2014, 136, 14554.
Flormann, et al., "The buckling instability of aggregating red blood cells," Scientifc Reports, 2017, 7, 7928.
Flormann, et al., "On the rheology of red blood cell suspensions with different amounts of dextran: Separating the effect of aggregation and increase in viscosity of the suspending phase," Rheologica Acta, 2016, 55, 477.
Rampling, "Interactions Between Dextran, Fibrinogen and Plasma Membranes," Biochemical Pharmacology, 1976, 25, 751.
Smith, et al., "Zeta potential: a case study of cationic, anionic, and neutral liposomes," Analytical and Bioanalytical Chemistry, 2017, 409, 5779.
Alsop, et al., "Swelling of phosphlipid membranes by divalent metal ions depends on the location of the ions in the bilayers," Soft Matter, 2016, 12, 6737.
Himbert, et al., "The Molecular Structure of Human Red Blood Cell Membranes from Highly Oriented, Solid Supported Multi-Lamellar Membranes," Scientific Reports, 2017, 7, 39661.
Liu, et al., "Erythrocyte-platelet hybrid membranes coating polypyrrol nanoparticles for enhanced delivery and photothermal therapy," Journal of Materials Chemistry B, 2018, 6, 7033.
Jiang, et al., Biomaterials, "Erythrocyte-cancer hybrid membrane-camouflaged melanin nanoparticles for enhancing photothermal therapy efficacy in tumors," Biomaterials 2019, 192, 292.

(56) References Cited

OTHER PUBLICATIONS

Laouini, et al., "Preparation, Characterization and Applications of Liposomes: State of the Art," Journal of Colloid Science and Biotechnology, vol. 1, 147-168 (2012).

Pedrosa, et al., "Research Paper; Plasma membrane targeting by short chain sphingolipids inserted in liposomes improves anti-tumor activity of mitoxantrone in an orthotopic breast carcinoma xenograft model," European Journal of Pharmaceutics and Biopharmaceutics (2015) (2015) 207-219.

Hoare, et al., Hydrogels in drug delivery: Progress and challenges,: Polymer 49 (2008) 1993-2007.

* cited by examiner

HYBRID BIOLOGICAL MEMBRANES, METHODS OF MAKING AND USES THEREOF

FIELD

The present invention relates to membranes, and in particular, to hybrid biological membranes and related methods and uses.

BACKGROUND

A biological membrane, biomembrane or cell membrane is a selectively permeable membrane that separates a cell from the external environment or creates intracellular compartments. Biological membranes, in the form of eukaryotic cell membranes, consist of a phospholipid bilayer with embedded, integral and peripheral proteins used in communication and transportation of chemicals and ions. The bulk of lipid in a cell membrane provides a fluid matrix for proteins to rotate and laterally diffuse for physiological functioning. Proteins are adapted to high membrane fluidity environment of lipid bilayer with the presence of an annular lipid shell, consisting of lipid molecules bound tightly to surface of integral membrane proteins.

Red blood cells (RBCs) or erythrocytes are the most common type of blood cell and the vertebrate's principal means of delivering oxygen (O2) to the body tissues—via blood flow through the circulatory system. RBCs take up oxygen in the lungs, or in fish the gills, and release it into tissues while squeezing through the body's capillaries.

The cytoplasm of erythrocytes is rich in hemoglobin, an iron-containing biomolecule that can bind oxygen and is responsible for the red color of the cells and the blood. Each human red blood cell contains approximately 270 million of these hemoglobin molecules. The cell membrane is composed of proteins and lipids, and this structure provides properties essential for physiological cell function such as deformability and stability while traversing the circulatory system and specifically the capillary network. RBC ghosts refer to RBCs in which the internal content of the RBCs has been removed. There have been attempts to use RBCs and RBCs ghosts as platforms for drug delivery.

Novel delivery platforms and methods involving biological membranes are desired.

SUMMARY

In accordance with an aspect, there is provided a hybrid biological membrane comprising an endogenous bilayer doped with one or more modifying lipid molecules.

In an aspect, the one or more modifying lipid molecules are fully saturated, partially saturated, or fully unsaturated.

In an aspect, the modifying lipids are endogenous or non-endogenous.

In an aspect, the modifying lipids are natural or non-natural.

In an aspect, the modifying lipids are synthetically produced.

In an aspect, the one or more modifying lipid molecules comprise phosphatidylcholine, phosphatidylserine, phosphatidylglycerol, phosphatidylethanolamine, phosphatidic acid, dimyristoylphosphatidylcholine, palmitoyloleoylglycerophosphocholine, palmitoyloleoylglycerophosphoserine, palmitoyloleoylglycerophosphoglycerol, sphingomyelin, phosphoethanolamine, a variant thereof, a derivative thereof, or a combination thereof, such as 1,2-dimyristoyl-sn-glycero-3-phoshatidylcholine (DMPC), 1-palmitoyl-2-oleoyl-glycero-3-phosphocholine (POPC), 1-palmitoyl-2-oleoyl-sn-glycero-3-phospho-L-serine (POPS), or 1-palmitoyl-2-oleoyl-sn-glycero-3-phospho-(1'-rac-glycerol) (POPG).

In an aspect, the ratio of endogenous bilayer lipids:modifying lipids is from about 1:10 to about 20:1, such as from about 1:4 to about 9:1, such as 1:4, 2:3, 1:1, 3:2, 4:1, or 9:1.

In an aspect, the modifying lipid molecules functionalize the biological membrane by altering its thickness, order, and/or surface charge.

In an aspect, the endogenous bilayer is an erythrocyte bilayer.

In an aspect, the membrane comprises a substantially stable symmetric distribution of synthetic lipids across the leaflets.

In an aspect, the modifying lipid molecules are substantially homogenously distributed into the endogenous bilayer.

In an aspect, the membrane comprises from about 5 mass % to about 50 mass % modifying lipid molecules, such as from about 10% to about 40%, such as about 20% or about 30%.

In an aspect, the membrane is biocompatible.

In an aspect, the membrane is resistant to mechanical and/or osmotic stress.

In an aspect, the membrane further comprises one or more biomolecules or small molecules.

In an aspect, the one or more biomolecules comprise proteins, nucleic acids, sugars, lipids, or a combination thereof.

In an aspect, the membrane encapsulates a releasable cargo.

In an aspect, the releasable cargo comprises a biomolecule or a small molecule.

In an aspect, the releasable cargo comprises a therapeutic agent, a prophylactic agent, a diagnostic agent, a marker agent, a prognostic agent, or a combination thereof.

In an aspect, the releasable cargo comprises an antibiotic.

In accordance with an aspect, there is provided a method of preparing a hybrid biological membrane, the method comprising doping an endogenous bilayer with one or more modifying lipid molecules.

In an aspect, the method further comprises purifying the endogenous bilayer prior to doping.

In an aspect, the method further comprises removing cellular contents from the endogenous bilayer prior to doping.

In an aspect, doping comprises mixing the endogenous bilayer with modifying lipid molecules.

In an aspect, the modifying lipid molecules are in the form of liposomes.

In an aspect, the method further comprising drying the hybrid biological membrane on a solid substrate having a lipid bilayer compatible surface.

In an aspect, drying the hybrid biological membrane comprises incubating the hybrid biological membrane on the solid substrate at a temperature of from about 0° C. to about 100° C. and a relative humidity of from about 0% to about 100%.

In an aspect, the solid substrate is hydrophilic.

In an aspect, the method further comprises incubating the hybrid biological membrane on the solid substrate to increase homogeneity of the hybrid biological membrane.

In an aspect, the endogenous bilayer lipids and the modifying lipid molecules anneal to form a substantially homogenous hybrid biological membrane structure.

In an aspect, the method further comprises rehydrating the hybrid biological membrane.

In an aspect, the endogenous bilayer comprises erythrocytes.

In an aspect, the erythrocytes comprise erythrocyte ghosts.

In an aspect, the one or more modifying lipid molecules comprise phosphatidylcholine, phosphatidylserine, phosphatidylglycerol, phosphatidylethanolamine, phosphatidic acid, dimyristoylphosphatidylcholine, palmitoyloleoylglycerophosphocholine, palmitoyloleoylglycerophosphoserine, palmitoyloleoylglycerophosphoglycerol, sphingomyelin, phosphoethanolamine, a variant thereof, a derivative thereof, or a combination thereof, such as 1,2-dimyristoyl-sn-glycero-3-phoshatidylcholine (DMPC), 1-palmitoyl-2-oleoyl-glycero-3-phosphocholine (POPC), 1-palmitoyl-2-oleoyl-sn-glycero-3-phospho-L-serine (POPS), or 1-palmitoyl-2-oleoyl-sn-glycero-3-phospho-(1'-rac-glycerol) (POPG).

In an aspect, the method further comprises incorporating one or more biomolecules or small molecules into the hybrid biological membrane.

In an aspect, the biomolecules comprise proteins, nucleic acids, sugars, lipids, or a combination thereof.

In an aspect, the method further comprises encapsulating a releasable cargo within the hybrid biological membrane, optionally during rehydration.

In an aspect, the releasable cargo comprises one or more biomolecules or small molecules.

In an aspect, the releasable cargo comprises a therapeutic agent, a prophylactic agent, a diagnostic agent, a marker agent, a prognostic agent, or a combination thereof.

In an aspect, the releasable cargo comprises an antibiotic.

In accordance with an aspect, there is provided a hybrid biological membrane prepared by the method described herein.

In accordance with an aspect, there is provided a tunable hybrid biological membrane for drug delivery, the membrane comprising a mixture of endogenous bilayer lipids and modifying lipids.

Other features and advantages of the present invention will become apparent from the following detailed description. It should be understood, however, that the detailed description and the specific examples, while indicating embodiments of the invention, are given by way of illustration only and the scope of the claims should not be limited by these embodiments, but should be given the broadest interpretation consistent with the description as a whole.

BRIEF DESCRIPTION OF THE DRAWINGS

Certain embodiments will now be described in greater detail with reference to the attached drawings in which.

DETAILED DESCRIPTION

Figure 1:
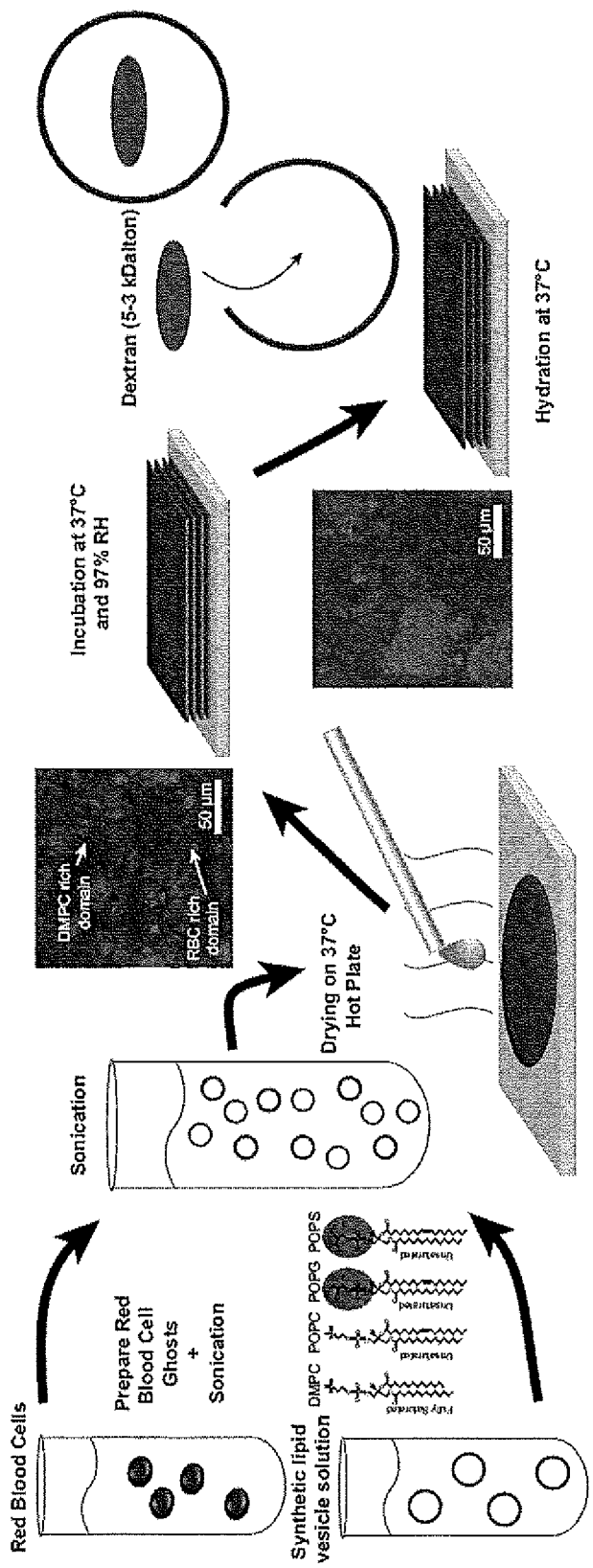
FIG. 1 shows the preparation of erythrocyte liposomes (ghosts) from human RBCs in an exemplary embodiment of the invention. Aqueous stock solutions of synthetic lipid molecules (dimyristoylphosphatidylcholine (DMPC), palmitoyloleoylglycerophosphocholine (POPC), palmitoyloleoylglycerophosphoserine (POPS) and palmitoyloleoylglycerophosphoglycerol (POPG)) were prepared. Blood and lipid solutions are sonicated before mixing in ratios: 1:4, 2:3, 1:1 3:2, 4:1 and 9:1. The resulting solution is sonicated 10 times in pulses of 55 s and applied onto a silicon wafer and allowed to dry and incubate. The wafer is immersed in a solution containing small molecules, which are encapsulated when hybrid erythrocyte liposomes form. In this work, fluorescein labeled dextran was incorporated. The insets show epi-fluorescent microscopic images of the wafer surface where protein rich, erythrocyte membrane rich areas are visible as lighter areas.

Described herein are hybrid biological membranes comprising an endogenous bilayer doped with one or more synthetic molecules. Further described are methods for the efficient preparation of hybrid biological membranes comprising an endogenous bilayer doped with one or more synthetic lipid molecules. The hybrid biological membranes described herein have tunable material properties by using different ratios or lipid classes. For example, the effect of different lipid classes including, but not limited, to phosphatidylcholine (PC), phosphoserine (PS), phosphoglycerol (PG), as well as varying degrees of saturation and tail length, on membrane morphology and structure was assessed using X-ray diffraction, molecular dynamics simulations and epi-fluorescent microscopy.

I. Definitions

Unless otherwise indicated, the definitions and aspects described in this and other sections are intended to be applicable to all aspects of the present invention herein described for which they are suitable as would be understood by a person skilled in the art.

In understanding the scope of the present disclosure, the articles "a", "an", "the", and "said" are intended to mean that there are one or more of the elements. Additionally, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

It will be understood that any aspects described as "comprising" certain components may also "consist of" or "consist essentially of," (or vice versa) wherein "consisting of" has a closed-ended or restrictive meaning and "consisting essentially of" means including the components specified but excluding other components except for materials present as impurities, unavoidable materials present as a result of processes used to provide the components, and components added for a purpose other than achieving the technical effects described herein. For example, a composition defined using the phrase "consisting essentially of" encompasses any known pharmaceutically acceptable additive, excipient, diluent, carrier, and the like. Typically, a composition consisting essentially of a set of components will comprise less than 5% by weight, typically less than 3% by weight, more typically less than 1% by weight of non-specified components.

It will be understood that any component defined herein as being included may be explicitly excluded by way of proviso or negative limitation, such as any specific compounds or method steps, whether implicitly or explicitly defined herein. For example, in aspects, polymers are excluded from the compositions described herein. For example, hydrogel polymers, such as PEG, may in aspects be excluded from the compositions described herein.

In addition, all ranges given herein include the end of the ranges and also any intermediate range points, whether explicitly stated or not.

The term "and/or" as used herein means that the listed items are present, or used, individually or in combination. In effect, this term means that "at least one of" or "one or more" of the listed items is used or present.

Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

II. Hybrid Biological Membrane

Described herein is a hybrid biological membrane comprising an endogenous bilayer doped with one or more modifying lipid molecules. Also described is a tunable hybrid biological membrane for drug delivery, the membrane comprising a mixture of endogenous bilayer lipids and synthetic lipids.

It will be understood that any modifying lipid molecules can be used herein and they can be, for example, fully saturated, partially saturated, or fully unsaturated. Various mixtures of saturated, unsaturated, and partially saturated lipids can be used in combination as desired to tune the membrane to have desired characteristics as described herein.

The modifying lipid molecules can be endogenous or non-endogenous. Typically, they are endogenous as this will be understood to improve biocompatibility of the resulting membrane structure. Further, the lipids may be naturally occurring or non-naturally occurring. In typical aspects, the lipids are synthetically produced but it will be understood that they could be extracted from natural sources if desired.

For example, the one or more modifying lipid molecules typically comprise phosphatidylcholine, phosphatidylserine, phosphatidylglycerol, phosphatidylethanolamine, phosphatidic acid, dimyristoylphosphatidylcholine, palmitoyloleoylglycerophosphocholine, palmitoyloleoylglycerophosphoserine, palmitoyloleoylglycerophosphoglycerol, sphingomyelin, or phosphoethanolamine. Variants and derivatives of these are explicitly contemplated as well as combinations. For example, the modifying lipids may comprise one or more of 1,2-dimyristoyl-sn-glycero-3-phosphatidylcholine (DMPC), 1-palmitoyl-2-oleoyl-glycero-3-phosphocholine (POPC), 1-palmitoyl-2-oleoyl-sn-glycero-3-phospho-L-serine (POPS), and 1-palmitoyl-2-oleoyl-sn-glycero-3-phospho-(1'-rac-glycerol) (POPG).

It will be understood that the endogenous bilayer comprises endogenous bilayer lipids and that the endogenous bilayer lipids and the modifying lipids may be used in any desired ratio with respect to each other in order to accomplish the desired hybrid biological membrane characteristics. For example, in some aspects, the ratio of endogenous bilayer lipids:modifying lipids is from about 1:10 to about 20:1, such as from about 1:4 to about 9:1, such as 1:4, 2:3, 1:1, 3:2, 4:1, or 9:1. These ratios are merely exemplary and can be adjusted to tune the resultant membrane as desired.

For example, the identity or identities of the modifying lipid molecules chosen for use herein, as well as their ratios, typically functionalize the biological membrane by altering its thickness, order, and/or surface charge. By choosing different modifying lipids and/or ratios thereof with respect to each other and/or the endogenous bilayer lipids, properties of the membrane can be finely tuned to achieve desired characteristics.

While any endogenous bilayer can be used, typically the endogenous bilayer is an erythrocyte bilayer. In more typical aspects, the bilayer is derived from erythrocyte ghosts. It will be understood that any eukaryotic membrane source can be used as the bilayer, such as from lung, kidney, liver, blood-brain-barrier, or placenta, for example.

The modifying lipids can be distributed symmetrically or asymmetrically across the leaflets of the bilayer. Typically, the membrane comprises a substantially symmetric distribution of synthetic lipids across the leaflets. Further, the symmetry of the distribution is typically substantially stable. While the modifying lipid molecules can be distributed in non-homogenous islands throughout the leaflets of the bilayer, typically the modifying lipid molecules are substantially homogenously distributed into the endogenous bilayer.

The modifying lipids may present in the membrane in any amount. In some aspects, the membrane comprises from about 5 mass % to about 50 mass % modifying lipid molecules, such as from about 5%, about 10%, about 15%, about 20%, about 25%, about 30%, about 40%, or about 45% to about 10%, about 15%, about 20%, about 25%, about 30%, about 40%, about 45%, or about 50%, such as from about 10% to about 40%, such as about 20% or about 30%.

The membrane described herein is typically biocompatible, in that it is compatible with the body of the subject to whom it is administered. This is typically due to the use of the endogenous bilayer, which typically is from the same species to which it is subsequently administered. Endogenous modifying lipids can also be used, which are unlikely to cause a negative immune reaction in the subject.

The membrane comprising endogenous bilayer lipids and modifying lipids may have characteristics that differ from a bilayer made solely from the endogenous bilayer lipids or one made solely from the modifying lipids. For example, typically the membrane is resistant to mechanical and/or osmotic stress.

The membrane may be further modified to include one or more biomolecules or small molecules. For example, the membrane, in addition to the endogenous bilayer lipids and modifying lipids described herein, may comprise proteins, nucleic acids, sugars, lipids, or a combination thereof. In one aspect, the membrane may contain a protein, such as an antibody, to target the membrane to a desired location in the body.

In additional or alternative aspects, the membrane encapsulates a releasable cargo. As the membrane is typically biocompatible and has a membrane structure surrounding a core, it serves as a suitable delivery vehicle for many different types of cargo. For example, the releasable cargo in aspects comprises a biomolecule or a small molecule. Examples include a therapeutic agent, a prophylactic agent, a diagnostic agent, a marker agent, a prognostic agent, or a combination thereof. For example, an antibiotic, a chemotherapeutic agent, an antibody, a fluorescent or MRI-imageable molecule, or combinations of any of these could be encapsulated by the membrane described herein.

III. Methods

Also described herein are methods of preparing a hybrid biological membrane. The method comprises doping an endogenous bilayer with one or more modifying lipid molecules. The endogenous bilayer and modifying lipid molecules are as described herein.

In aspects, the endogenous bilayer is purified prior to doping it with the modifying lipid molecules. The endogenous bilayer may also be processed to remove its cellular contents prior to doping. This can be accomplished by washing and/or sonicating as described herein and/or as known in the art. For example, if the endogenous bilayer is an erythrocyte bilayer, the cellular contents can be removed to result in an erythrocyte ghost. Exemplary methods of obtaining erythrocyte ghosts are described in the examples herein and other methods are known to a skilled person.

In aspect, the endogenous bilayer is doped with the modifying lipid molecules by mixing the endogenous bilayer and modifying lipids. The modifying lipids may be in any form but are typically in liposomes.

Once the endogenous bilayer is doped with the modifying lipid molecules, the mixture is typically dried on a solid substrate having a lipid bilayer compatible surface, such as a hydrophilic surface, under suitable conditions. For example, the suitable conditions may comprise a temperature of from about 0° C. to about 100° C., such as from about 0° C., about 10° C., about 20° C., about 30° C., about 40° C., about 50° C., about 60° C., about 70° C., about 80° C., or about 90° C. to about 10° C., about 20° C., about 30° C., about 40° C., about 50° C., about 60° C., about 70° C., about 80° C., about 90° C., or about 100° C. Additionally or alternatively, the suitable conditions may comprise a relative humidity of from about 0% to about 100%, such as from about 0%, about 10%, about 20%, about 30%, about 40%, about 50%, about 60%, about 70%, about 80%, or about 90% to about 10%, about 20%, about 30%, about 40%, about 50%, about 60%, about 70%, about 80%, about 90%, or about 100%.

During drying or a subsequent incubation step, the method in aspects results in an increase in homogeneity of the hybrid biological membrane. In aspects, the endogenous bilayer lipids and the modifying lipids anneal to form a substantially homogenous hybrid biological membrane structure.

Once the endogenous bilayer is doped with the modifying lipid molecules and dried, it is typically stored dried or it is rehydrated for storage and/or at the time of use. During rehydration, the membrane that is substantially flat on the solid surface begins to bleb, producing the final hybrid biological membrane.

As described above, the biomolecules or small molecules may be incorporated into the membrane. This can be accomplished before, during, and/or after the drying or rehydrating steps. If a cargo is desired to be encapsulated within the core of the membrane structure, this is typically done during rehydration, as the cargo can be incorporated into the blebs of membrane that are released from the solid surface.

It will be understood that membranes produced by the methods described herein are also contemplated.

EXAMPLES

The following non-limiting examples are illustrative of the present invention:

Example 1. Hybrid Erythrocyte Liposomes: Functionalized Red Blood Cell Membranes for Molecule Encapsulation Abstract The modification of erythrocyte membrane properties provides a new tool towards improved drug delivery and biomedical applications. We present the fabrication of hybrid erythrocyte liposomes by doping red blood cell membranes with synthetic lipid molecules of different classes (PC, PS, PG) and different degrees of saturation (14:0, 16:0-18:1). The respective solubility limits were determined, and material properties of the hybrid liposomes were studied by a combination of X-ray diffraction, epi-fluorescent microscopy and Molecular Dynamics (MD) simulations. Membrane thickness and lipid orientation can be tuned through the addition of phosphatidylcholine lipids. The hybrid membranes can be fluorescently labelled by incorporating Texas-red DHPE, and their charge modified by incorporating phosphatidylserine and phosphatidylglycerol. By using fluorescein labeled dextran as an example, we demonstrate that small molecules can be encapsulated into these hybrid liposomes.

Introduction

The target-oriented drug delivery is one of the biggest challenges in modern drug development. The idea of using carriers to transport and release drug molecules at specific locations in the body is intriguing, and can significantly increase the drug's efficiency and reduce potential side effects [1-4]. Hydrogels and synthetic liposomes are two common attempts to address this problem [5, 6]. Despite their success, these non-endogenous drug carriers raise numerous challenges: The efficiency is often limited by the host's immune response [6] or requires costly implants [5].

First proposed by Ihler et. al. [7], Red blood cells (RBCs) have been in focus as potential drug carriers. The evident advantage of using RBCs are an extended natural lifespan of these cells within the body, a greater biocompatibility and a direct access to numerous target sites [8]. With glucocorticoid analogue dexamethasone loaded RBCs, the first RBC based therapy reached the clinical stage [9] as treatment of Ataxia-telangiectasia, a rare neurodegenerative disease [10]. The two common approaches described in the literature aim to encapsulate drugs and molecules within erythrocyte ghosts or attach reactive agents to RBCs [11-13]. For instance, Thrombomodulin [12] and plasminogen activators [11, 13] have been successfully linked to RBCs resulting in an increased circulation time of these molecules [11-14]. *Escherichia coli* L-asparaginase loaded erythrocytes have been reported to show a 10 times increase of the pharmacodynamic of this therapeutic enzyme in mice [15]. Although RBCs have numerous advantages over aforementioned synthetic drug carriers, loaded RBCs or RBC ghosts typically lack of specificity with respect to target sites or show a reduced biocompatibility [16, 17]. To address these difficulties, recent approaches used hybrid RBC liposomes as drug carriers [18], or combined membranes from multiple endogenous cells [19, 20].

In this example, we describe the preparation of hybrid erythrocyte liposomes and study the effect of different lipid classes (PC, PS and PG), as well as varying degrees of saturation and tail length (14:0, 16:0-18:1), on the material properties of RBC membranes. First, empty RBC liposomes, often referred to as RBC ghosts, were mixed with synthetic liposomes, sonicated and dried on a solid support. This two dimensional confinement promotes the fusion of both membrane species during the subsequent incubation. Hybrid liposomes were formed by re-hydrating the dry membranes. Small molecules can be incorporated within these hybrid liposomes during this step. A sketch of the preparation protocol is shown in FIG. 1.

Molecular level structural and dynamical information was obtained using X-ray diffraction, epi-fluorescent microscopy and Molecular Dynamics (MD) simulations. Dimyristoylphoshatidylcholine (DMPC) for instance was found to increase the degree of order while decreasing the membrane thickness. In contrast, palmitoyloleoylglycerophosphocholine (POPC) lowers the overall bilayer thickness and reduces the degree of order. Anionic lipids, such as palmitoyloleoylglycerophosphoserine (POPS) and palmitoyloleoylglycerophospho-glycerol) (POPG), were used to alter the membranes' charge and result in a decreased Zeta-potential. On microscopic scales, synthetic lipid molecules fuse homogeneously with erythrocyte membranes when within their solubility limits. MD simulations, however, indicate the presence of dynamic nanometer sized erythrocyte rich and erythrocyte poor domains, mimicking rafts in biological plasma membranes.

RESULTS

Figure 2:
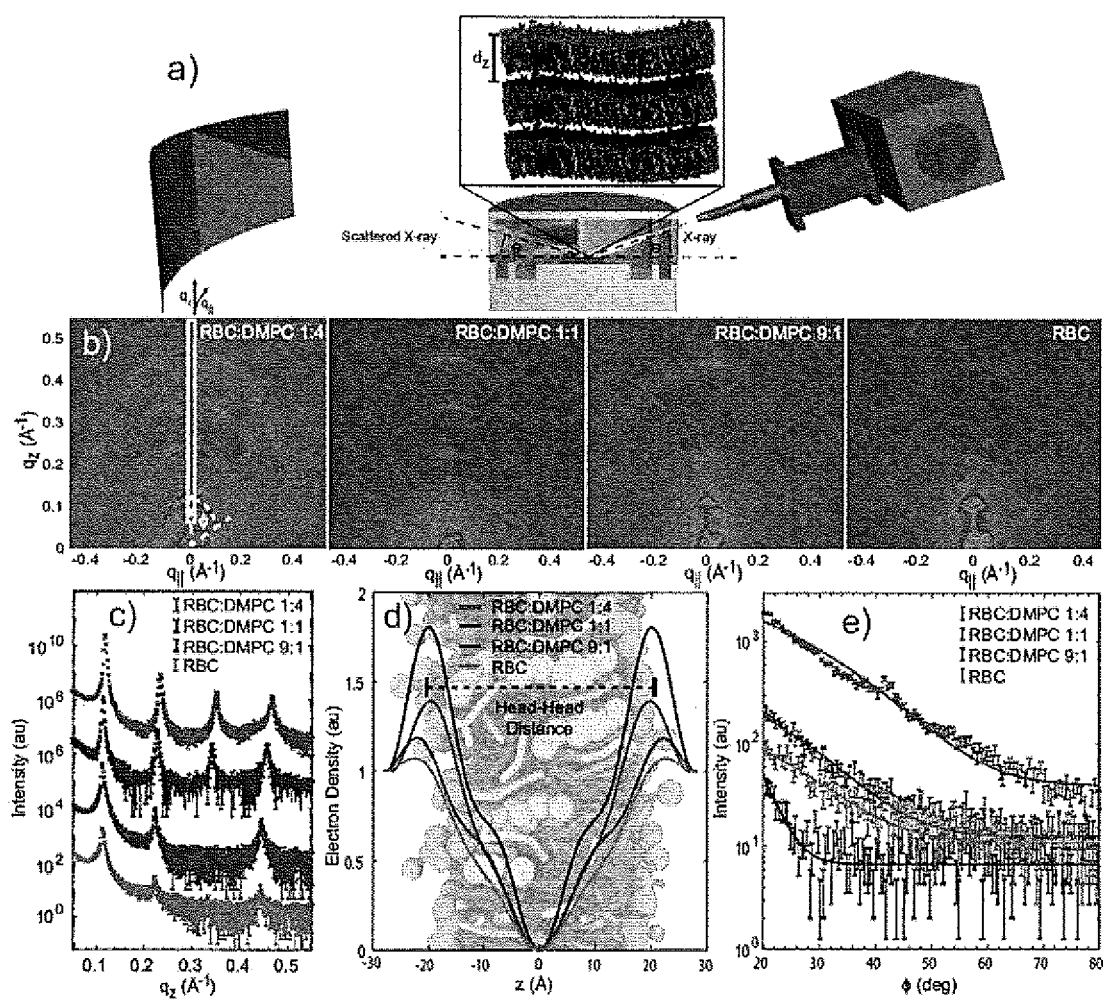
FIG. 2 shows the molecular structure of hybrid erythrocyte membranes as determined by X-ray diffraction in exemplary embodiments of the invention. a) The experimental setup using exemplary solid supported membranes placed in a humidity-controlled chamber at 88% relative humidity. The sample remains horizontal throughout the measurement. $q_z$ measures out-of-plane structure while $q_\parallel$ measures in-plane structure. b) 2-dimensional X-ray intensity maps for three exemplary RBC:DMPC hybrid samples: 1:4, 1:1 and 9:1. The scattering pattern of pure RBC membranes are included as reference. Bright prominent spots are apparent, which appear as series of Bragg-peaks in c) a line-cut along $q_z$ at $q_\parallel=0$ and are result of the lamellar spacing between the stacked membranes. d) The corresponding electron density data determined by a 1-dimensional Fourier Analysis. The head groups show up as increased electron density around $|z|\sim20$ Å. e) The degree of orientation was determined by fitting a Gaussian profile to the scattered intensity along the meridional angle $\phi$ and using Herman's orientation function.

Molecular Structure of Hybrid Membranes:

The molecular structure of the hybrid erythrocyte membranes, prepared as depicted in FIG. 1, was determined by Xray diffraction. The measurements were performed on solid supported membranes after incubation but before liposomal fabrication. Scans were done in a humidity and temperature controlled chamber. The setup is depicted in FIG. 2*a*). FIG. 2*b*) shows 2-dimensional X-ray intensity maps for erythrocyte membranes containing DMPC at ratios of (RBC:DMPC) 1:4, 1:1 and 9:1. Pure RBC membranes are shown as reference. The observed Bragg peaks are the result of the membrane stacking. The 1:4 sample mainly consists of synthetic DMPC and forms a well pronounced series of peaks. The intensity and number of these peaks decrease as the RBC concentration increases, indicative of a less-well-ordered lamellar phase with increased mosaicity. Line-cuts along $q_\parallel=0$ were calculated by integration along the marked rectangle and are shown in FIG. 2c). The lamellar spacing, $d_z$, was determined from the distance of the reflectivity Bragg peaks using Bragg's law, $d_z=2\pi/q_z$.

Electron densities perpendicular to the membranes are presented in FIG. 2d), as calculated from a 1-dimensional Fourier analysis. The data show an increased electron density around $|z|\sim20$ Å, corresponding to the electron-rich head groups of the lipid molecules, and a decreased density in the center of the bilayer ($|z|=0$ Å). The membrane thickness was determined by the distance between the two maxima in the electron density profile, and will be referred to as head-to-head distance dim. FIG. 2e) shows the result of an angular integration along the dotted line in FIG. 2b). A small width in the angular distribution is indicative of well-ordered membranes within the stack. The degree of order is quantified by fitting Herman's orientation function. A degree of orientation between ~82% and ~97% was determined, in good agreement with previous studies on pure red blood cells [21], and on mono- or multicomponent synthetic membranes [22].

Figure 3:
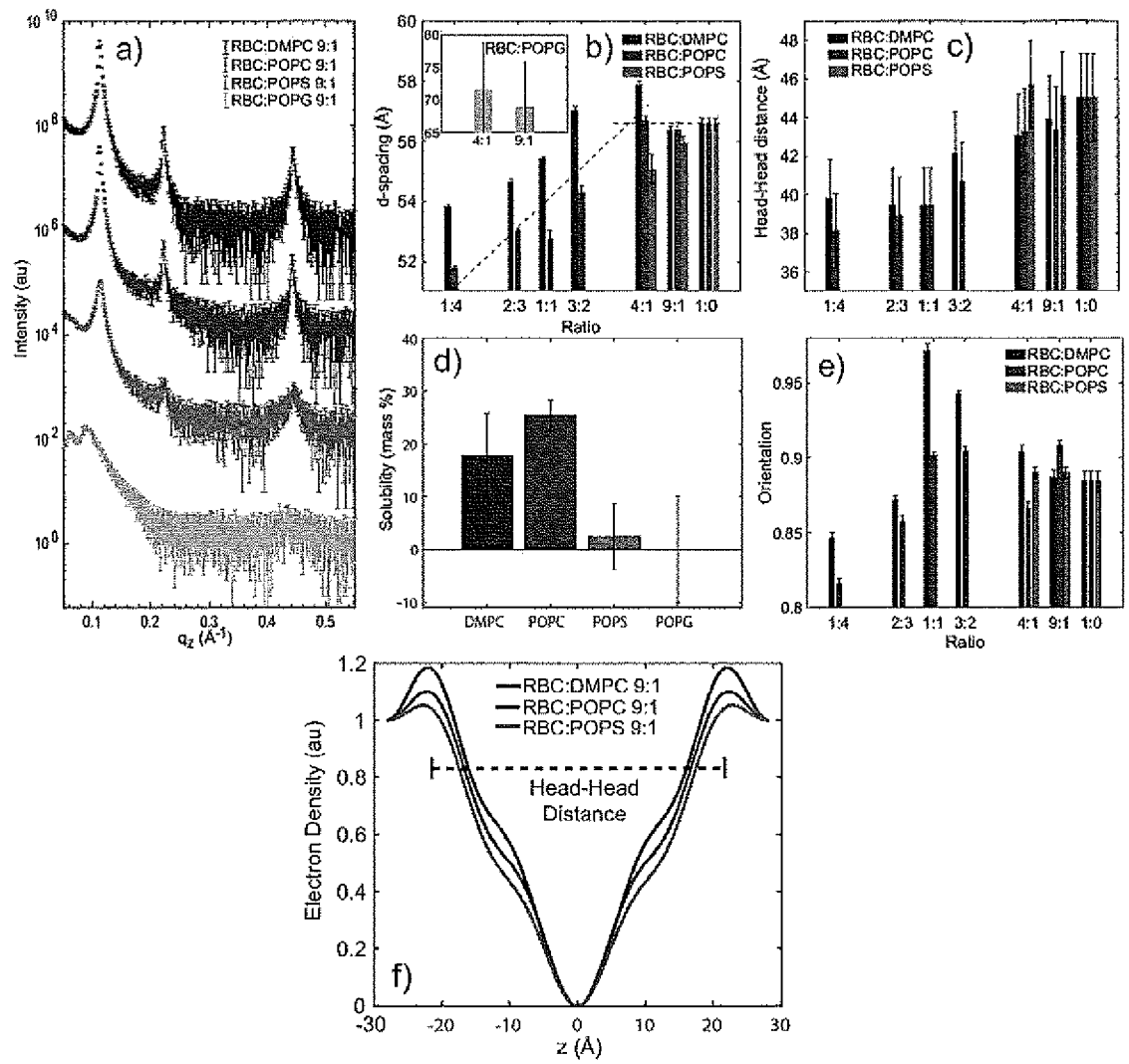
FIG. 3 shows membrane molecular structure characterization using different types of synthetic lipids in exemplary embodiments of the invention. a) Line-cut along $q_z$ for exemplary hybrid membranes containing 10 mass percent synthetic lipids (DMPC, POPC, POPS and POPG). b) Lamellar spacing $d_z$ as function of synthetic lipid concentration for the prepared lipid species. c) Corresponding Head-head distance as function of the synthetic lipid concentration. d) The degree of order as function of the synthetic lipid concentration and species determined by Herman's orientation function. e) The solubility lipid was determined by the intercept of two linear regimes fitted to part b). f) Corresponding electron density to a) determined by a 1-dimensional Fourier analysis. The fits are shown as dotted lines in the case of POPC.

FIG. 3a) compares the reflectivity of different types of synthetic lipids, all at a ratio of 9:1. While the inclusion of DMPC and POPC was found to lead to well organized membranes, the addition of POPS and POPG significantly suppressed higher order peaks, indicative of increased disorder. The corresponding electron densities are shown in FIG. 3O and are in agreement with increasing tail disorder between DMPC-POPC-POPS (no electron density could be determined for the case of POPG because of the absence of higher order Bragg peaks).

DMPC, POPC and POPS show a gradual increase in lamellar spacing and head-head distance with an increasing fraction of RBC membranes, as shown in FIGS. 3b) and c). It converges to ~56 Å for the $d_z$-spacing and ~44 Å for the head-head distance, in good agreement with previously published measurements on red-blood cell membranes [21].

Two regimes were observed for all lipid species: a linearly increasing regime and a plateau region for higher fractions of RBC membranes. The latter one indicates minor structural differences as compared to a pure erythrocyte membrane. Consequently, we define the solubility limit as the boundary between both regimes. It was determined for all lipid molecules by fitting lines to both regimes and determining the x-coordinate of the intersect. The fits are indicated in FIG. 3b) by dotted lines using POPC as an example. The solubility limits are plotted in FIG. 3d).

FIG. 3e) compares the membranes' orientation as function of the synthetic lipid concentration and the lipid species. The highest degree of orientation was observed for an equal ratio between erythrocyte and synthetic lipids, while a high concentration of synthetic lipids causes an overall lower degree of orientation. Values for DMPC are significantly higher as compared to POPC and POPS, as fully saturated lipid molecule seem to induce additional order in the erythrocyte membrane.

Molecular Dynamics (MD) Simulation

Figure 4:
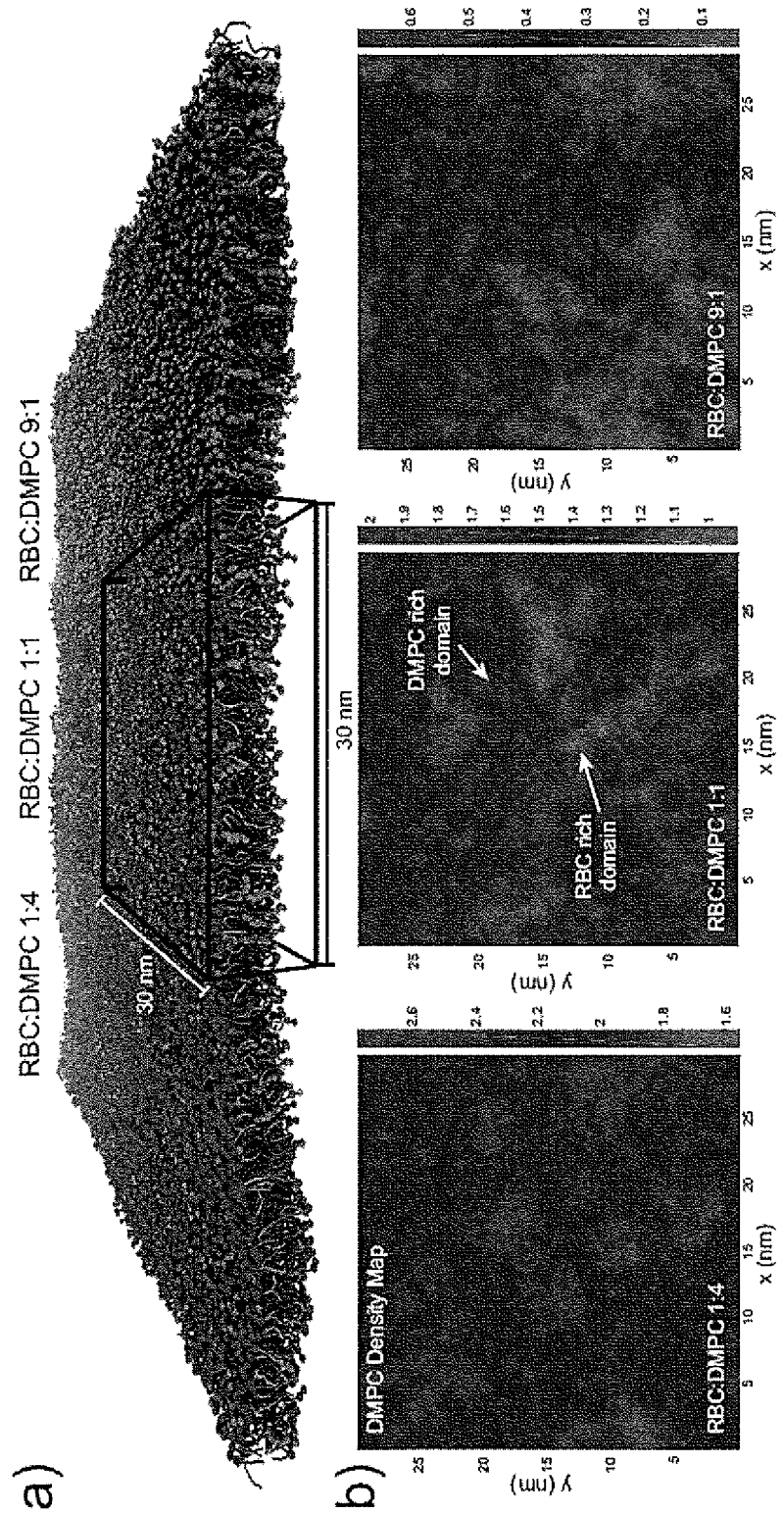
FIG. 4 shows molecular dynamics simulations of membranes in an exemplary embodiment of the invention. a) Snapshot of MD simulation at t=5 μs. The phosphate group is indicated by red and blue spheres, corresponding to RBC and DMPC lipids respectively. Cholesterol is represented by yellow spheres. Gray and light blue lines represent the lipid tails of RBC and DMPC lipids respectively. The simulation box is shown as black box and measures 30×30 nm. Water molecules are omitted for clarity. b) DMPC density maps for the simulated hybrid membranes containing 80, 50 and 10 mass % DMPC. Dark areas correspond to a high concentration of DMPC while the lighter regions correspond to a DMPC depletion, i.e. a high concentration of RBC lipid species.

Experiments point to a homogeneous mixing of erythrocyte and synthetic membranes. MD simulations give information about the underlying dynamical processes. Coarse grained MD simulations were performed using erythrocyte membranes containing 10 mol % (~11.5 mass %), 50 mol % (~54 mass %) and 80 mol % (~82.4 mass %) DMPC to study the dynamics and in-plane organization of the hybrid membranes. Snapshots after 5 μs of simulation time are depicted in FIG. 4a). Red and blue spheres represent the phosphate groups of lipid molecules assigned to the red blood cell fraction and synthetic DMPC lipids respectively. Cholesterol is depicted by yellow spheres. The snapshots indicate a homogeneous mixture of both membrane species. This changes when comparing the time averaged density of the lipid molecules, as shown in FIG. 4b), where dynamic small, nanometer sized patches become visible.

The size of the erythrocyte and DMPC patches can be determined by counting the number of pixels above the median density multiplied with the resolution. Patch sizes ranging from 35.3 nm$^2$ to 147.0 nm$^2$ were determined, as listed in Table 1. These patches are dynamic entities and undergo molecular fluctuations, which mimic the natural fluctuations observed in biological plasma membranes.

TABLE 1

DMPC domain sizes were determined from 2-dimensional density maps by counting the number of pixels above a threshold and multiplying the results with the resolution.

| Membrane System | DMPC domain size (nm$^2$) | |
| --- | --- | --- |
| | Upper Leaflet | Lower Leaflet |
| RBC:DMPC 1:4 | 75.4 | 95.2 |
| RBC:DMPC 1:1 | 46.1 | 147.0 |
| RBC:DMPC 9:1 | 79.0 | 35.3 |

Liposome Characterization and Encapsulation of Molecules

Figure 5:
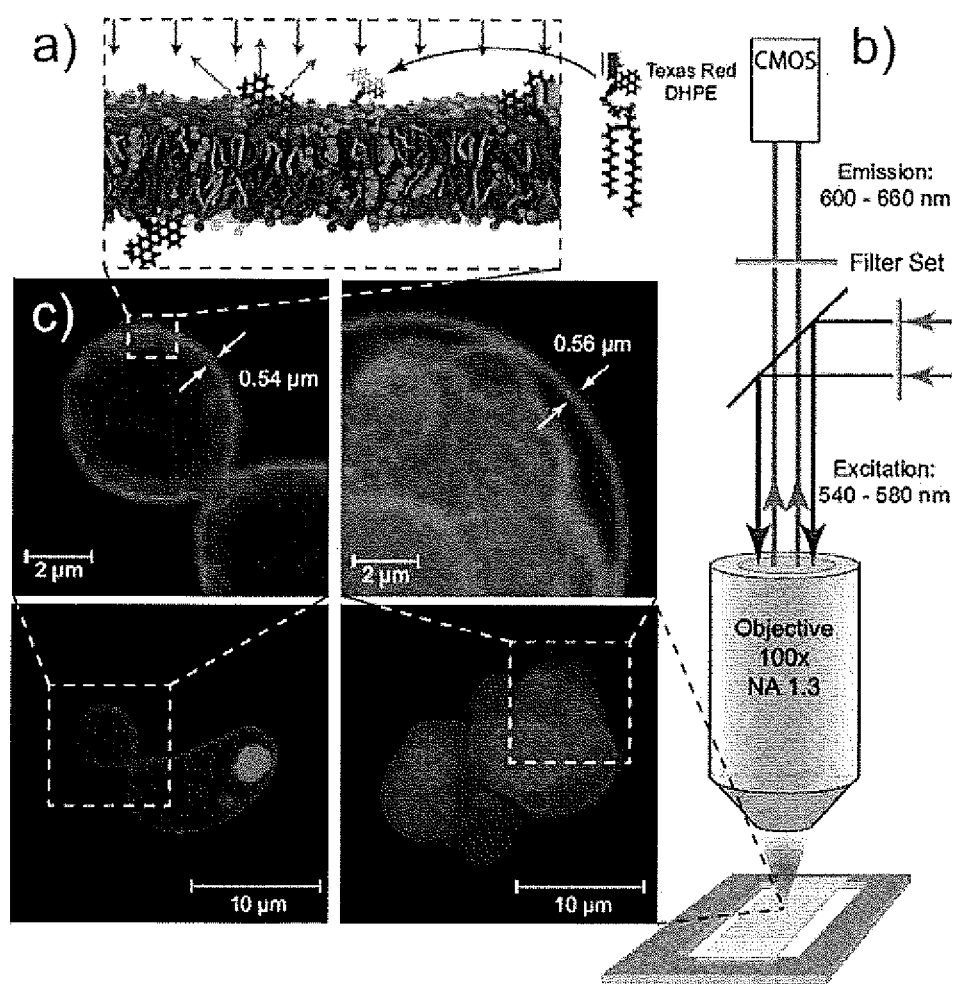
FIG. 5 shows fluorescence characterization of hybrid liposomes in an exemplary embodiment of the invention. a) Exemplary liposomes containing 0.5 mass % head-group labeled Texas red DHPE were prepared. b) The Epi-fluorescent microscope uses an excitation filter of 540-580 nm and an emission filter of 600-660 nm. c) The membrane of the liposomes shows up as a bright, red barrier under the microscope. Complex liposomes structures were observed consisting of multiple fused spherical objects. The membrane thickness was found to be 560 nm, the resolution limit of the setup.

Fluorescently labeled hybrid liposomes (FIG. 5a)) were visualized using an epifluorescent microscope (FIG. 5b)). Liposomes had a typical size of 10-15 μm and varied in shape, as shown in FIG. 5c). The membrane appears as a bright red edge with a width of ~550 nm, within the resolution limit of the microscopic setup used. The liposomes in FIG. 5c) appear to be homogeneously labeled and show no indication of phase separation or domain formation within the resolution limit of the microscope.

Figure 6:
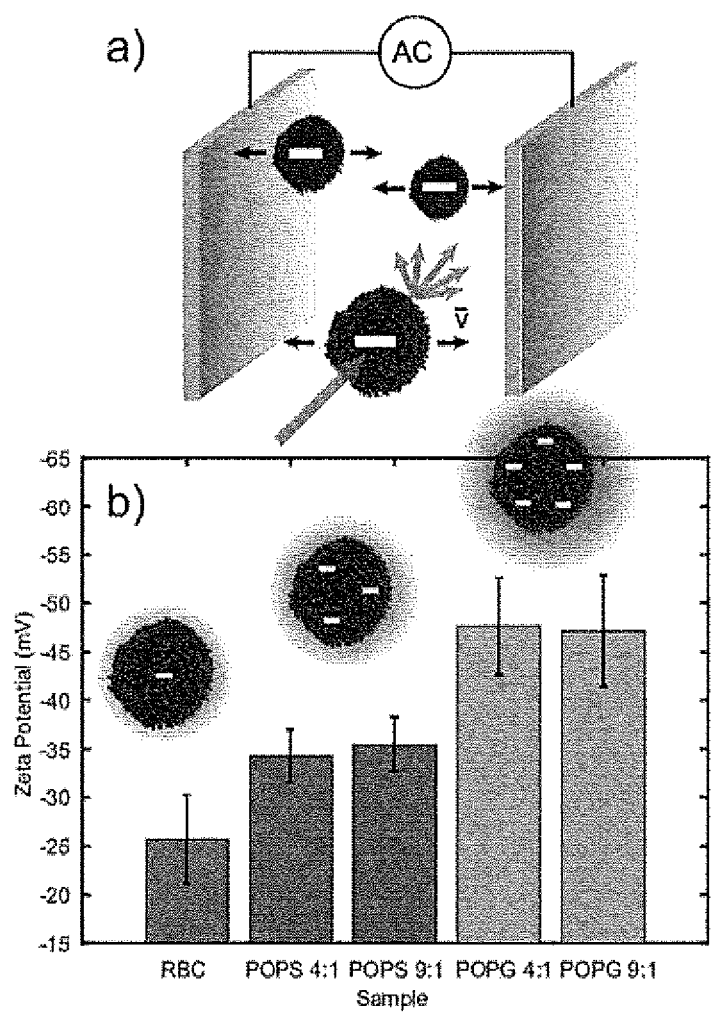
FIG. 6 shows Zeta-potential characterization of hybrid liposomes in an exemplary embodiment of the invention. a) The Zeta-potential of the prepared hybrid liposomes was determined using a Zetasizer Nano ZS from Malvern Panalytical. Alternating current is applied via two electrodes allowing the measurement of charge-dependent dynamics of the liposomes. b) Zeta-potential for RBC ghosts and hybrid liposomes containing 10 and 20 mass % POPS and POPG, respectively. Both synthetic lipid species add additional charge to the membrane.

Size and size distribution of all hybrid liposomes were determined using DLS and are listed in Table 2. Liposomes were sonicated before the measurements for better comparison. The average diameter ranges from ~120 nm to ~208 nm. While pure RBC liposomes (ghosts) showed an average size of ~200 nm, inclusion of saturated and charged lipids resulted in smaller sized liposomes. The inclusion of dextran led to a small increase of the liposome size. While the size distribution of pure RBC liposomes was found to be reasonably well defined, as indicated by the polydispersity index, the inclusion of synthetic lipids increased the size distribution in all cases. DMPC and POPC resulted in a significant broadening of the distribution while adding charged lipids (POPS and POPG) increased the distribution moderately, only. The Zeta-potential was determined for pure RBC ghosts as well as for hybrid membranes containing 10% and 20% POPS and POPG. By applying an alternating current, the Zeta-potential is a measurement of potential charge-dependent dynamics of the liposomes, as depicted in FIG. 6a). Both anionic lipids decrease the Zeta-potential, as shown in FIG. 6b). While erythrocyte membranes show a Zeta-potential of −25.7±5 mV, POPS and POPG were found to lower the potential to −35.5±5 mV and −47.5±5 mV, respectively. Previous studies [23] have reported a linear relationship between the concentration of charged lipid molecules and the Zeta-potential. However, these data show no concentration dependence, within statistical errors.

TABLE 2

The diameter of the hybrid liposomes after sonication determined
by dynamic light scattering (DLS). The average diameter ranges
from ~120 nm to ~208 nm. Inclusion of saturated and charged lipids
resulted in smaller sized liposomes. The inclusion of dextran led
to a small increase of the liposome size. While the size distribution
of pure RBC liposomes is reasonably well defined,
as indicated by the polydispersity index, the inclusion of synthetic
lipids increased the size distribution in all cases.
DMPC and POPC resulted in a significant
broadening of the distribution while adding charged lipids
(POPS, POPG) increased the distribution moderately only.

| Liposomes | Diameter (nm) | Polydispersity Index |
|---|---|---|
| Pure ghosts | 199.05 ± 3.34 | 0.14 ± 3.34 |
| RBC:DMPC 4:1 | 147.8 ± 2.3 | 0.32 ± 0.04 |
| RBC:DMPC 9:1 | 198.9 ± 12.1 | 0.42 ± 0.06 |
| RBC:POPC 4:1 | 208.0 ± 8.8 | 0.48 ± 0.079 |
| RBC:POPC 9:1 | 174.5 ± 6.7 | 0.46 ± 0.01 |
| RBC:POPS 4:1 | 164.3 ± 1.0 | 0.174 ± 0.02 |
| RBC:POPS 9:1 | 147.9 ± 1.35 | 0.218 ± 0.004 |
| RBC:POPG 4:1 | 138.3 ± 1.6 | 0.241 ± 0.003 |
| RBC:POPG 9:1 | 147.2 ± 1.1 | 0.248 ± 0.008 |
| RBC:DMPC 4:1 with Dextran | 160.0 ± 60 | 0.3 ± 0.08 |
| RBC:POPG 4:1 with Dextran | 119.3 ± 1.46 | 0.245 ± 0.01 |

Figure 7:
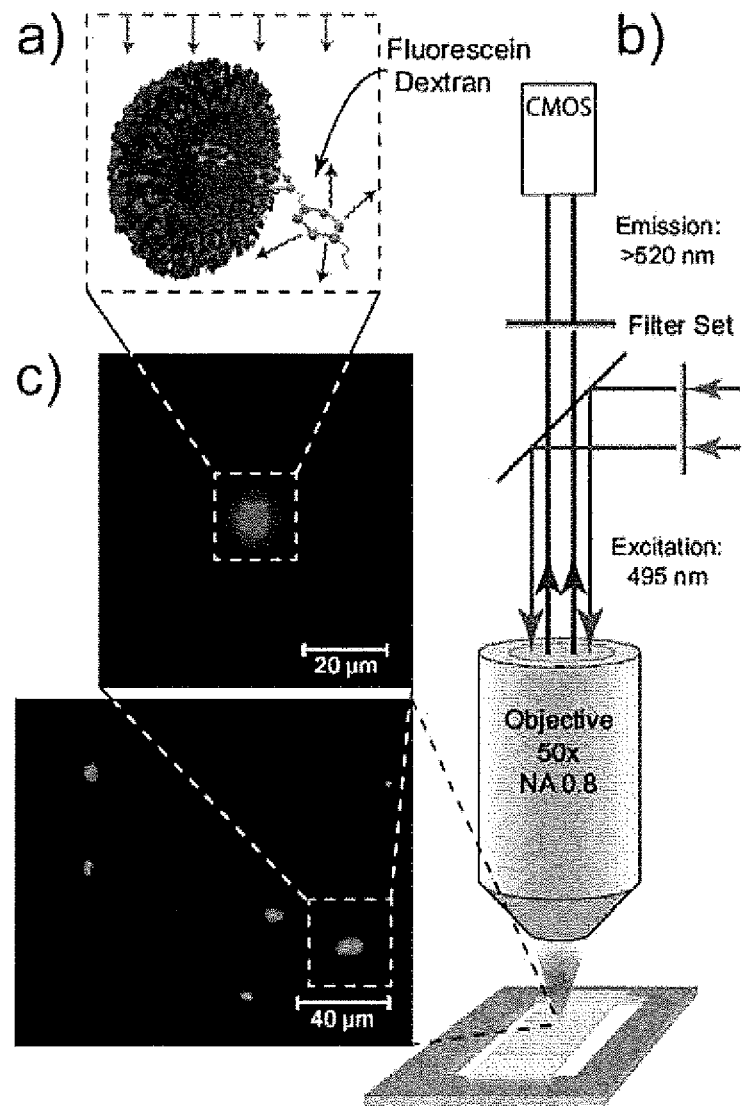
FIG. 7 shows fluorescent images of hybrid liposomes containing a small molecule in an exemplary embodiment of the invention. a) Exemplary hybrid liposomes were filled with fluorescein labeled dextran. b) Epi-fluorescent microscopic image of the prepared liposomes, which light up as bright spots on the image. c) The experimental setup consisted of an epi-fluorescent microscope with an excitation wavelength of 495 nm and a long-pass analysis filter with a barrier wavelength of 520 nm.~20 μl of the liposome solution was applied to a microscope slide and sealed by a cover slip.

Molecules were encapsulated in the hybrid liposomes by hydrating the solid supported membranes in an aqueous solution, as pictured in FIG. 7a). The experimental setup is shown in FIG. 7b). FIG. 7c) shows liposomes that were prepared in a 1 mg/ml solution of 3-5 kDa fluorescein labeled dextran. The interior of the liposomes lights up in green under the microscope indicating that the dextran is located within the hybrid liposomes. Dextran has been previously reported to interact with the RBC membrane at larger concentration of dextran (>10 mg/ml) [24-26]. The homogeneous color and intensity of the liposomes, however, indicate that the molecules are homogenously distributed within the liposomes (within the resolution limit of the microscope).

Discussion

Endogenous substances can transport drugs hidden from the immune system and allow the design of far more complex liposomes. However, controlling membrane morphology and structure is essential in generating applicable carrier systems. Human erythrocytes are well suited as a base for such hybrid liposomes as their membrane can be easily isolated from other cellular components. At the same time, they have the potential of minimizing immune reactions and circulating in the blood stream for extended periods of time.

The protocol presented herein allows the efficient preparation of hybrid erythrocyte membranes. The data indicate that synthetic lipid molecules can be homogenously incorporated into RBC membranes, which is a significant improvement over previously published protocols [18]. The crucial intermediate step in the protocol is the preparation of solid supported hybrid membranes. The 2-dimensional confinement together with drying and incubation promotes the fusion of both membrane species. While microscopy is a very efficient tool to determine the topology of hybrid membranes and liposomes, X-ray diffraction gives access to nanoscale bulk information. Experiments were complemented by computer simulations, which can now model plasma membranes realistically [27], and provide important information on nanoscopic dynamics and mixing.

The lack of split peaks in the X-ray diffraction measurements, together with the homogeneous red color of the fluorescently labeled hybrid liposomes indicate a homogenous fusion of both membrane species. A deeper insight into the mixing is provided by MD simulations. While snapshots of the simulation indicate a uniform mixture of erythrocyte and synthetic membranes, the time averaged density maps show evidence for dynamic nanometer sized patches of erythrocyte rich and poor regions.

Previous MD simulations on large scale models show a similar de-mixing of lipid species in biological cell membranes. Ingolfsson and co-authors also demonstrated that these patches form and disappear on nano to microsecond time scales [27]. It is now widely accepted that local fluctuations are an intrinsic property of membranes [27-31]. These fluctuations typically average out on longer length and time scales leading to a uniform membrane structure. The observed small dynamic domains are, therefore, not the result of a static phase separation between both membrane species but the result of nanoscopic molecular fluctuations, typically observed in biological membranes.

It is noted that erythrocyte membranes are in general asymmetric [32]. POPS for instance is exclusively found in the inner leaflet of mammalian cell membranes. PE lipids are located on both leaflets with a preferred position on the inner leaflet. In experiments, RBC ghosts in general co-exist in inside-out and right-side out configurations, as discussed for example in [33]. When the ghosts are dried out on the solid support there is a random stacking of the different membrane orientations and the resulting membrane layer and liposomes are on average symmetric with respect to the composition of the inner and outer leaflets. Therefore, conclusions on effects due to potential asymmetry of the hybrid membranes and liposomes cannot be made. MD models were prepared by first modeling an asymmetric RBC membrane. Synthetic lipids were then equally added to both leaflets to mimic the experimental conditions. There was, however, no evidence for an asymmetric distribution of the synthetic lipids between the two leaflets within the 5 μs of simulation time, which could for instance be caused by lipid flip-flop. A stable symmetric distribution of synthetic lipids across the leaflets is therefore assumed.

While up to 30 mass % DMPC and POPC can be mixed with erythrocyte membranes, smallest amounts of charged lipids disturb the membrane assembly resulting in decreased (POPS) and increased (POPG) lamellar spacings, and the formation of smaller liposomes. In particular POPG inhibits the assembly of stacked membranes. These findings are supported by the DLS and Zeta-potential measurements. Inclusion of synthetic lipids (except for RBC:POPC 4:1) resulted in smaller sized liposomes, indicating a reduced stability. Inclusion of dextran led to a small increase of the liposome size.

While the Zeta-potential is not a direct measure of the charge density, as detailed in the paper by Bhattacharjee [34], it determines the interfacing potential of the so-called slipping plane around the liposome. The Zeta-potential of the erythrocyte membrane was measured to be −25.7±4.6 mV, in good agreement with previous studies [35]. POPS and POPG further decrease the Zeta-potential to −34.3±2.7 mV and −35.5±2.8 mV and −47.7±5 mV and −47.1±5.8 mV, respectively, indicating an increased negative membrane charge. Previous studies reported a concentration-dependent decrease of the Zeta-potential in the presence of PS [23] and PG [35] lipids in synthetic membranes. The concentration dependent differences in the measurements, however, are within the statistical errors.

Liposomes can be loaded with molecules during the re-hydration phase, when the molecule containing solution is applied onto the dried out supported membranes. The molecules are then encapsulated when the membranes rehydrate and liposomes form. The loading efficiency is defined as the amount of encapsulated molecules relative to the initial concentration of the molecule, and was determined using UV-vis spectroscopy. An encapsulation efficiency of 2.1±0.7% for dextran in hybrid liposomes containing 20% DMPC and 3.5±0.5% for hybrid liposomes containing 20% POPG was determined. Both efficiencies are comparable, in the order of a few percent and are only slightly smaller than typical loading efficiencies reported for synthetic liposomes of <10% [36].

Figure 8:
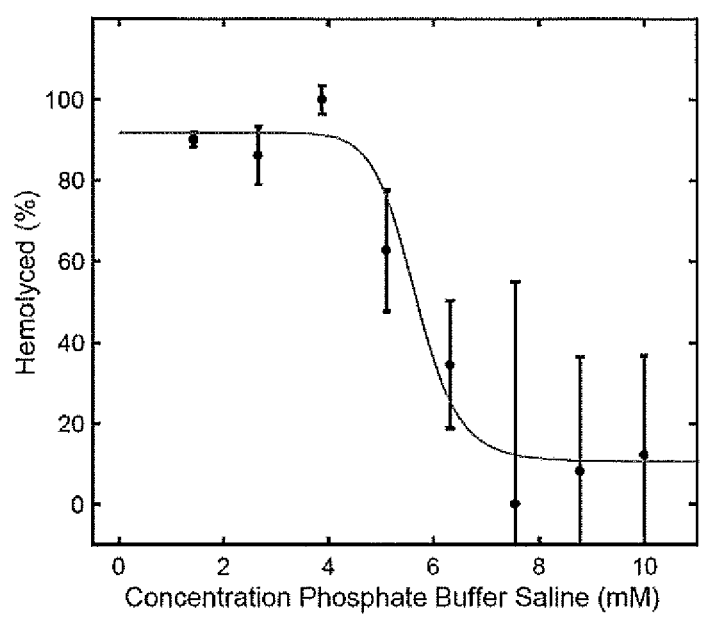
FIG. 8 shows a lysis curve for hybrid liposomes containing 20% DMPC in an exemplary embodiment of the invention. The liposomes were prepared in a PBS solution containing 1 mg/ml fluorescein labeled dextran. The liposomes were then exposed to mechanical and osmotic stress by placing the liposomes in a solution with varying concentrations of phosphate buffer saline. The increase of lysed hybrid liposomes below 5.6 mM phosphate buffer saline is in good agreement with results for pure RBC.

The biocompatibility of RBC based drug delivery systems is a long standing concern. While the hybrid membranes are entirely composed of biocompatible materials [18], previous studies have shown that loading of RBCs can have a significant impact on their biocompatibility [16, 17]. This is, however, often a result of heavy modifications to the RBC surface. The longevity of modified RBC depends on numerous mechanisms and has been studied in detail [37-40]. However, a key factor for the biocompatibility is the resilience of the hybrid liposomes against mechanical stress. FIG. 8 shows the result of a lysis assay where hybrid liposomes containing 20% DMPC were exposed to increasing osmotic stress by altering the molar concentration of a phosphate buffer saline. This method has previously been described as in-vitro test for biocompatibility of RBC membranes [41]. The data show an increase of lysed hybrid liposomes below 5.6 mM phosphate buffer saline, corresponding to a ~150 mOsm solution, in good agreement with results for pure RBC [41]. It can, therefore, be expected that the hybrid liposomes will behave similar to RBCs in-vivo since these results prove the biocompatible nature of these hybrid liposomes.

In summary, hybrid erythrocyte membranes were prepared by purifying and doping endogenous RBC bilayers with synthetic lipid molecules. The impact of different lipid classes (PC, PS and PG), as well as different tail saturation (14:0, 16:0-18:1), on membrane morphology and structure was assessed using X-ray diffraction, MD simulations and epi-fluorescent microscopy. Fluorescently labeled hybrid liposomes were prepared using Texas-red DHPE (TR-DHPE) and fluorescein labeled dextran. Different synthetic lipid species functionalize the RBC membranes by altering their thickness, order and the surface charge. As fully saturated lipid, DMPC was found to induce additional order, while POPC led to a more disordered bilayer with increased mosaicity. Both lipids result in a significantly reduced membrane thickness. The addition of POPS and POPG led to the formation of charged liposomes, as proven by a decreased Zeta-potential.

Experimental and computational findings indicate a homogenous mixing of erythrocyte and synthetic membranes down to the nanoscale. Formation of dynamic nanometer sized patches of constantly mixing and de-mixing erythrocyte rich and poor domains was, however, observed as a result of molecular fluctuations. By using dextran as an example, it is shown that small molecules can be encapsulated into the hybrid liposomes.

Experimental Methods and Procedures

Preparation of hybrid membrane mixtures: The preparation is based on a protocol first published by Himbert et al. [21]. All blood samples were collected using sodium heparin coated venous blood collection tubes from BD (Product Number: BD 367874). The blood was washed twice and the RBC were isolated as described in [21]. Hemolysis was induced by adding 50 µl of the hematocrit to 1 ml of a diluted buffer solution in a 1.5 ml reaction tube. This buffer is prepared by mixing 16 ml of Phosphate Buffered Saline (PBS) with 484 ml of 18 MΩ·cm ultra-pure water and adjusting the pH to a value of 8 by slowly adding potassium hydroxide. The reaction tubes were immediately stored on ice to prevent a fast re-closing of the ruptured cells. This enables the removal of hemoglobin and other cellular compartments using multiple washing steps as demonstrated in [21]. The protocol results in a white pellet containing empty RBC liposomes. The pellets from 24 reaction tubes were combined and the volume was adjusted to 0.5 ml resulting in a ghost concentration of ~14 mg/ml [21]. The resulting solution was tip sonicated 20 times for 5 s each at a power of 100 W. Note, that the reaction tube was placed on ice during sonication to prevent the sample from overheating. Afterwards, the tube was centrifuged for 15 min at 20,000 g. The supernatant consists of a solution of small nanometer-sized liposomes [21], referred to as Blood Solution. Aqueous solutions of dispersed 1,2-dimyristoyl-sn-glycero-3-phosphatidylcholine (DMPC), 1-palmitoyl-2-oleoyl-glycero-3-phosphocholine (POPC), 1-palmitoyl-2-oleoyl-sn-glycero-3-phospho-L-serine (POPS) and 1-palmitoyl-2-oleoyl-sn-glycero-3-phospho-(1'-rac-glycerol) (POPG) were prepared by dissolving 14 mg of each lipid in 1 ml of 18 MΩ·cm ultra-pure water. The resulting solution was tip sonicated 20 times for 10 s each at a power of 100 W until the solutions were clear. This sonicated solution will be referred to as Lipid Solution. For DMPC and POPC, assays at ratios of (Blood Solution:Lipid Solution) 1:4, 2:3, 1:1, 3:2, 4:1, and 9:1 were prepared. For POPS and POPG, both solutions were mixed in ratios of 4:1 and 9:1. The reaction tube with the final solution was placed on ice and tip sonicated 20 times for 5 s each. Fluorescently labeled membranes were prepared by doping the bilayers with Texas Red 1,2-Dihexadecanoyl-sn-Glycero-3-Phosphoethanolamine (TR-DHPE) (Thermo Fisher, Catalog number: T1395MP) which was used previously as an indicator for liquid disordered ld domains [42-45]. TR-DHPE was reported for its interaction with lipid molecules, such as DPPC [46], resulting in a reduced diffusion coefficient [46], and induced domain formation [47] at higher concentrations (>0.2 mol %). 1 mg of TR-DHPE was dissolved in 1 ml chloroform. 5.6 mg of DMPC (this corresponds to hybrid membranes containing 40 mass % DMPC) was dissolved in 1 ml chloroform. 52 µl of the TR-DHPE solution was mixed with the DMPC solution in a glass vial. Chloroform was removed by blowing dry $N_2$ gas in the glass vial for ~20 minutes before mixing the sample with ultra-pure water and tip sonicating 20 times for 10 s each at a power of 100 W. The concentration of TR-DHPE corresponds to 0.5 mol % in the Lipid Solution and 0.003 mass % when mixed with erythrocyte membranes. This solution will be referred to as Fluorescent Solution. For the stained membrane assays, the Fluorescent Solution was mixed with 80 µl of the Blood Solution creating a 3:2 sample.

Figure 9:
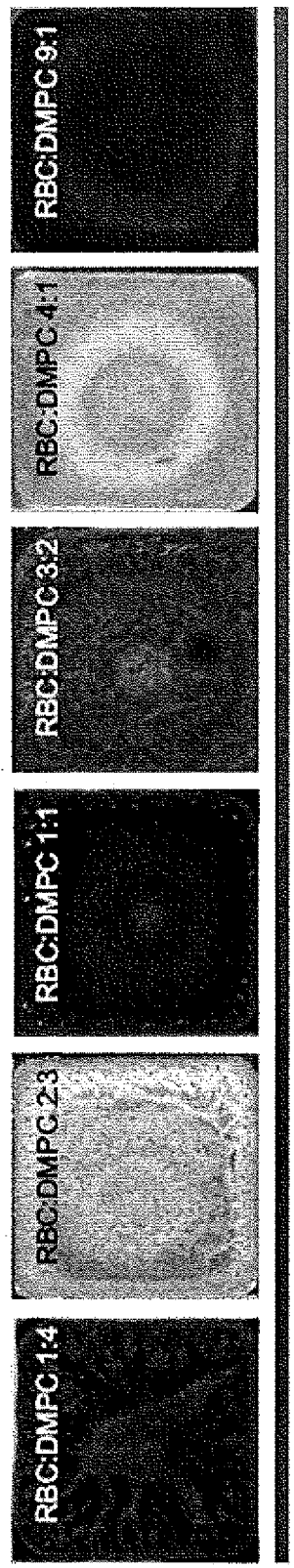
FIG. 9 shows images of prepared silicon wafers coated with hybrid membranes containing 10, 20, 50, 60, and 80% DMPC as exemplary embodiments of the invention.

Preparation of Liposomes: The preparation of liposomes is a two-step process. First, erythrocyte ghosts and synthetic liposomes were mixed and sonicated. The solution was then applied to a surface, slowly dried, and incubated. The resulting solid supported membranes initially show large, micrometer sized erythrocyte and synthetic domains as depicted in FIG. 1. During incubation, the large domains merge to form homogenous hybrid membranes. Membranes were applied onto single-side polished silicon wafers. 100 mm diameter, 300 µm thick silicon wafers were pre-cut into 10×10 mm² chips. The wafers were functionalized with a solution of 15 ml sulfuric acid and 5 ml hydrogen peroxide (Piranha solution) resulting in a hydrophilic surface. This strong oxidizing agent removes all organic contaminants on the surface, but do not disturb the native silicon oxide layer. Each wafer was then thoroughly rinsed with ~50 mL of ultra pure water with a resistance of 18.2 MΩ·cm and placed on a hot plate (37° C.) in a 3-dimensional orbital shaker. 100 µl of the hybrid membrane solution was pipetted slowly onto the wafer. The sample was covered with a tilted lid of a petri dish and allowed the membrane solution to slowly dry within ~12 h. The dried wafers were then incubated at 97% relative humidity and 37° C. by placing the samples in a sealed container with a saturated $K_2SO_4$ solution. This allows the erythrocyte and synthetic membrane domains to fuse into a homogenous membrane phase, as shown in FIG. 1. Sample pictures of different RBC-DMPC ratios are shown in FIG. 9. Liposomes were then synthesized by placing the silicon wafers in a reaction tube filled with 2 ml of ultra-pure water. The tubes were then bath sonicated for 1 h at 37° C. This re-hydrates the membrane stack and let the membranes bleb, leaving a blank silicon wafer. The resulting solution had a concentration of ~7 mg/ml of membrane material. Liposomes were characterized by dynamic light scattering (DLS) and the determination of the Zetapotential, as detailed below. To encapsulate molecules within the liposomes, the solid supported membranes were placed in 2 ml of an aqueous solution of 1 mg/ml fluorescein dextran and bath sonicated at 37° for ~1 hour. The sample was then centrifuged for 20 minutes at 20,000 g. The supernatant was removed and replaced with ultra-pure water. This washing step was repeated twice to isolate the stained liposomes. The resulting solution was applied onto a microscope slide and covered with a coverslip prior to imaging. Liposomes prepared by this protocol showed a large polydispersity index (PDI). Measurements performed on pure RBC liposomes determined an average size of 481.0±11.41 nm and a PDI of 0.53. This can be optimized by an additional tip sonication (20 times for 5 s each at a power of 100 W) of the liposomes resulting in an average size of 199.05±3.34 with a PDI of 0.14±3.34.

X-ray diffraction experiment: X-ray scattering data was obtained using the Biological Large Angle Diffraction Experiment (BLADE) in the Laboratory for Membrane and Protein Dynamics at McMaster University. BLADE uses a 9 kW (45 kV, 200 mA) CuKα rotating anode at a wavelength of 1.5418 Å using a Rigaku HyPix-3000 2D semiconductor detector with an area of 3,000 mm² and 100 µm pixel size [48]. All samples were prepared and measured in replicates to check for consistency. Both source and detector are mounted on movable arms such that the membranes stay horizontal during the measurements. Focusing multi-layer optics provides a high intensity parallel beam of ~200 µm with monochromatic X-ray intensities of up to $10^8$ counts. Note that there is no risk of sample damage using this in-house technique because of the relatively low intensity of the X-ray beam as compared to synchrotron sources. The samples were mounted in a custom-built humidity chamber during the experiments to control the humidity of the membranes. The result of an X-ray experiment is a 2-dimensional intensity map of a large area of the reciprocal space, as sketched in FIGS. 2a) and b), covering length scales from about 2.5 to 100 Å. All scans were measured at 28° C. and 88% relative humidity (RH) hydration. As depicted in FIG. 2a), the wafers were oriented in the X-ray diffractometer, such that the $q_∥$-axis probed lateral structure, parallel to the wafer surface, and the perpendicular axis, $q_z$, probed out-of-plane structure, perpendicular to the substrate. The out-of-plane structure of the membrane was determined using specular reflectivity. The relative electron density, ρ(z), is approximated by a 1-dimensional Fourier analysis [49].

$$\rho(z) = \frac{2}{d_z} \sum_{n=1}^{N} \sqrt{I_n q_n}\, v_n \cos\left(\frac{2\pi n z}{d_z}\right) \quad (1)$$

where N is the highest order of the Bragg peaks observed. $F(q_n)$ is known as the form factor and is determined by multiplying the integrated peak intensity $I_n$ with $q_n$ [49] and is in general a complex quantity. In case of centro-symetrie, the form factor becomes real and the phase problem of crystallography, therefore, simplifies to the sign problem $F(q_z)=\pm|F(q_z)|$. An X-ray diffraction experiment probes the form factor at discrete values of $q_z$, and continuous function, $T(q_z)$, can be fitted to the data [49].

$$T(q_z) = \sum_{n=1}^{N} \sqrt{I_n q_n}\, v_n \operatorname{sinc}\left(\frac{1}{2}d_z q_z - \pi n\right) \quad (2)$$

Once an analytical expression for $T(q_z)$ has been determined from fitting the experimental peak intensities, the phases $v_n$ can be assessed from $T(q_z)$. The phase array $v_n=[-1\ -1\ 1\ -1\ 1]$ was used for all samples. The electron densities determined by Eq. (1) are on a relative scale. In order to compare the electron densities in FIG. 2d) and 30, ρ in the membrane center at z=0 was set to 0 and the electron density at the boundaries, which probe the water layer between the stacked membranes, were scaled to 1. To determine the degree of orientation of the membranes in the stack, the correlation peak intensities were integrated as function of the meridonal angle φ (the angle relative to the $q_z$ axis) as depicted in FIG. 2b). The corresponding intensity was fit with a Gaussian distribution centered at 0, which was then used to calculate the degree of orientation using Hermans orientation function:

$$H = \frac{3 <\cos^2(\delta)> - 1}{2} \quad (3)$$

The experimental errors were determined as follows: Errors for peak positions, peak width and peak height are determined as the fit standard errors, corresponding to 95% confidence bounds, equivalent to 2 standard deviations, a. Errors for calculated parameters, such as peak area, were then calculated by applying the proper error propagation.

Figure 10:
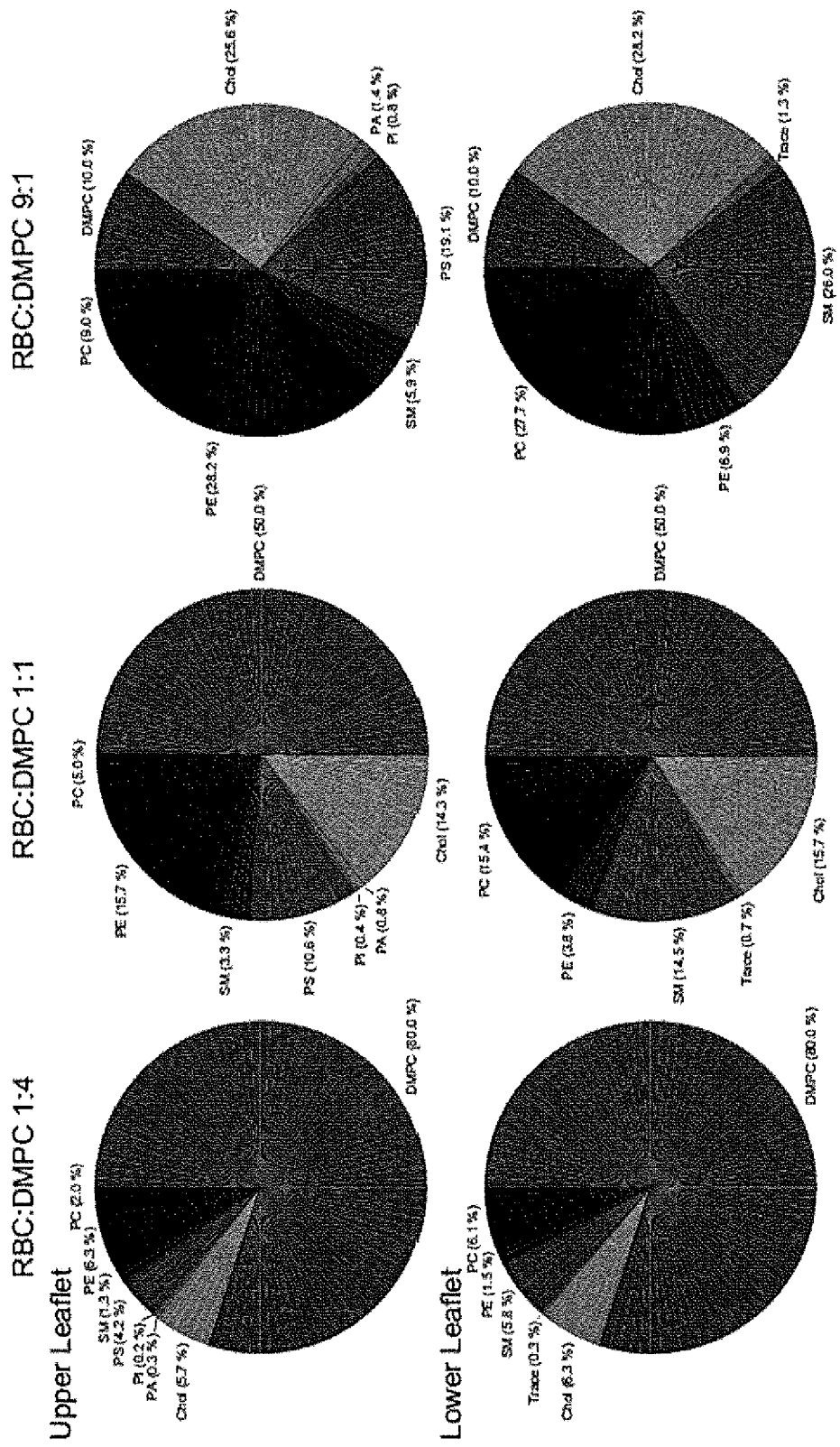
FIG. 10 shows relative concentrations of lipid species within the simulated membrane patches in an exemplary embodiment of the invention.

Molecular Dynamics Simulation: MD simulations were performed on MacSim, a GPU accelerated computer workstation using GROMACS Version 5.1.4. The computer is equipped with a 40 Core central processing unit (CPU, Intel® Xeon® CPU ES-2630 v4 @ 2.20 GHz), 130 GB random-access memory (RAM) and three graphic processing units (GPU, 2×NVIDIA 1080 TDI+1×GeForce GT 730). Seven membrane models were designed using the CHARMM-GUI membrane-builder (http://charmm-gui.org/)[50, 51] and the Martini forcefield 2.2 [51]. The systems correspond to a pure red blood cell membrane and membranes containing 10, 50, and 80% DMPC respectively. Each system represents a membrane patch of 30×30 nm with 1500 lipid molecules on each leaflet and 37 water molecules per lipid representing a fully hydrated state of the membrane. The lipid composition of the membrane patch was chosen according to the widely accepted experimental findings by Dodge et al. [32]. However, the presented lipodomic analysis is limited to the ratio of lipid classes and tail saturation. Thus further approximations to the overall lipid composition had to be made. The same lipid species presented in the work by Ingolfsson and co-workers [27] was used and concentrations adapted respectively to match the aforementioned experimental findings [32]. Note that multiple lipid species are represented by the same arrangement of atoms in the coarse-grained martini force field. Each membrane system was charge-neutralized by the addition of (NaCl or KCl) counterions. Simulations were equilibrated for 5 ns using an NPT ensemble (constant pressure and temperature), and then run for 5 μs. Only the final 3 μs were analyzed, after affirming the membrane had reached equilibrium by determining the area per lipid. Prior to each simulation run, the system was allowed to equilibrate for simulated 5 ns. All simulations used a 2 fs time step, a short range van der Waal cutoff of 1.1 nm, a potential-shift-verlet coulomb modifier and periodic boundary conditions were applied to all spacial directions. Neighbor lists were updated in intervals of 20 steps. The temperature coupling was controlled by a v-rescale thermostat at a constant pressure of 1 bar using Parrinello-Rahman semi-isotropic weak coupling ($\tau$=12 ps; compressibility $\beta=3\cdot10^{-4}$ bar$^{-1}$). DMPC density maps were calculated using the gmx densmap function provided by GROMACS. For this purpose, the phosphate group of DMPC was indexed for each leaflet respectively and the density map was averaged over the last microsecond of the simulation. The pure RBC membrane model contained 55 different lipid species from 5 different lipid classes. However, the exact composition was adjusted to produce the desired hybrid membrane models. FIG. 4a) shows a 3-dimensional render of membranes containing 10, 50 and 80 mol % DMPC. The lipids tails are represented by cyan and gray bonds for DMPC and RBC lipids, while blue and red spheres highlight the phosphate group of each membrane species respectively. Details about the exact lipid composition of each model can be found in Table 3. FIG. 10 visualizes the relative concentrations of lipid species in the membrane model. Time-resolved DMPC density were determined by averaging the in-plane DMPC density over 1 μs between 2 μs and 5 μs in steps of 100 ns. The data were visualized using Matlab and were rendered with ffmpeg (Version 2.8.15).

TABLE 3

Number concentration of lipid molecules within the simulated coarse grained RBC membrane model.

| Layers | Species | RBC: DMPC 1:4 | | RBC: DMPC 1:1 | | RBC: DMPC 9:1 | |
|---|---|---|---|---|---|---|---|
| | | upper | lower | upper | lower | upper | lower |
| PC Lipids | POPC | 10 | 31 | 26 | 79 | 46 | 141 |
| | DOPC | 1 | 3 | 2 | 7 | 4 | 12 |
| | PIPC | 15 | 46 | 38 | 116 | 68 | 208 |
| | PEPC | 1 | 2 | 1 | 5 | 3 | 8 |
| | PAPC | 2 | 7 | 6 | 18 | 11 | 33 |
| | DAPC | 0 | 1 | 1 | 2 | 1 | 4 |
| | PUPC | 1 | 2 | 1 | 5 | 3 | 8 |
| PE Lipids | POPE | 23 | 6 | 56 | 14 | 102 | 25 |
| | DOPE | 0 | 0 | 0 | 0 | 0 | 0 |
| | PIPE | 15 | 4 | 38 | 9 | 68 | 17 |
| | PQPE | 4 | 1 | 9 | 2 | 17 | 4 |
| | PAPE | 21 | 5 | 52 | 13 | 93 | 23 |
| | DAPE | 21 | 5 | 52 | 12 | 90 | 22 |
| | PUPE | 8 | 2 | 19 | 5 | 34 | 8 |
| | DUPE | 4 | 1 | 9 | 2 | 17 | 4 |

TABLE 3-continued

Number concentration of lipid molecules within the simulated coarse grained RBC membrane model.

| Layers | Species | RBC: DMPC 1:4 | | RBC: DMPC 1:1 | | RBC: DMPC 9:1 | |
|---|---|---|---|---|---|---|---|
| | | upper | lower | upper | lower | upper | lower |
| Sphingomyelin | DPSM | 9 | 39 | 23 | 97 | 41 | 175 |
| | DBSM | 4 | 18 | 10 | 44 | 18 | 79 |
| | DXSM | 6 | 28 | 15 | 69 | 28 | 125 |
| | POSM | 0 | 0 | 0 | 1 | 0 | 1 |
| | PGSM | 0 | 0 | 0 | 1 | 0 | 1 |
| | PNSM | 0 | 1 | 0 | 2 | 1 | 4 |
| | BNSM | 0 | 0 | 0 | 1 | 0 | 2 |
| | XNSM | 0 | 1 | 0 | 2 | 1 | 3 |
| PS Lipids | POPS | 1 | 0 | 3 | 0 | 6 | 0 |
| | PIPS | 5 | 0 | 13 | 0 | 23 | 0 |
| | PQPS | 8 | 0 | 20 | 0 | 37 | 0 |
| | PAPS | 35 | 0 | 88 | 0 | 158 | 0 |
| | DAPS | 1 | 0 | 3 | 0 | 6 | 0 |
| | PUPS | 11 | 0 | 29 | 0 | 51 | 0 |
| | DUPS | 1 | 0 | 3 | 0 | 6 | 0 |
| PI Lipids | POPI | 0 | 0 | 1 | 0 | 1 | 0 |
| | PIPI | 1 | 0 | 1 | 0 | 2 | 0 |
| | PAPI | 1 | 0 | 2 | 0 | 4 | 0 |
| | PUPI | 0 | 0 | 1 | 0 | 2 | 0 |
| PA Lipids | POPA | 2 | 0 | 4 | 0 | 7 | 0 |
| | PIPA | 1 | 0 | 3 | 0 | 6 | 0 |
| | PAPA | 1 | 0 | 3 | 0 | 6 | 0 |
| | PUPA | 1 | 0 | 1 | 0 | 3 | 0 |
| Others | PPC | 0 | 2 | 0 | 0 | 0 | 9 |
| | OPC | 0 | 1 | 0 | 0 | 0 | 3 |
| | IPC | 0 | 1 | 0 | 0 | 0 | 3 |
| | APC | 0 | 1 | 0 | 0 | 0 | 3 |
| | UPC | 0 | 0 | 0 | 0 | 0 | 1 |
| Cholesterol | | 85 | 94 | 214 | 235 | 384 | 423 |
| RBC | | 300 | 300 | 750 | 750 | 1350 | 1350 |
| DMPC | | 1200 | 1200 | 750 | 750 | 150 | 150 |

Epi-fluorescent microscopy: Hybrid liposomes were visualized on a Nikon Eclipse Ti2-E inverted microscope, equipped with a CFI Plan Fluor 100 Oil immersion objective with a numerical aperture of 1.30 and a Tu Plan Fluor BD 50× objective with a numerical aperture of 0.8. The instrument was used in episcopic illumination mode using a X-Cite 120 LED combined with an excitation filter of 540-580 nm and an emission filter of 600-660 nm. Images were taken with an Andor Zyla 5.5 sCMOS camera with a resolution of 2560×2160 pixels and a pixel size of 6.5 μm and processed by cropping the image to the size of the liposomes shown. For each picture, brightness and contrast has been adjusted using ImageJ (Version 1.52i). Edges were detected in ImageJ and the contrast was further increased by adding both the original data and the edge detected picture.

Dynamic light scattering and determination of the Zeta-potential: The size distribution and the Zeta-potential of the prepared liposomes were determined on a Zetasizer Nano ZS from Malvern Panalytical. The instrument utilizes a 4 mW He—Ne laser (Wavelength: 633 nm) in combination with a non-invasive backscattering optics to measure a dynamic light scattering (DLS) spectrum allowing the diffusion constant D of the liposomes to be determined. This is related to the particle size via the Stokes-Einstein relation: $D=K_B T/6\pi\eta r$, where $\eta$ is the dynamic viscosity of the solution, $K_B$ is the Boltzmann Constant, T is the sample temperature and r is the radius of a presumably spherical particle. The Zeta-potential is determined by Laser Doppler Micro-Electrophoresis. Here, an alternating electric field is applied to the solution and the velocity of the particles is determined via the patented phase analysis light scattering (M3-PALS, U.S. Pat. No. 7,217,350). This allows for the determination of the charge dependent mobility of the particles. All measurements were performed at 25° C. on 1 ml sample containing ~14 mg/ml of membrane material.

Figure 11:
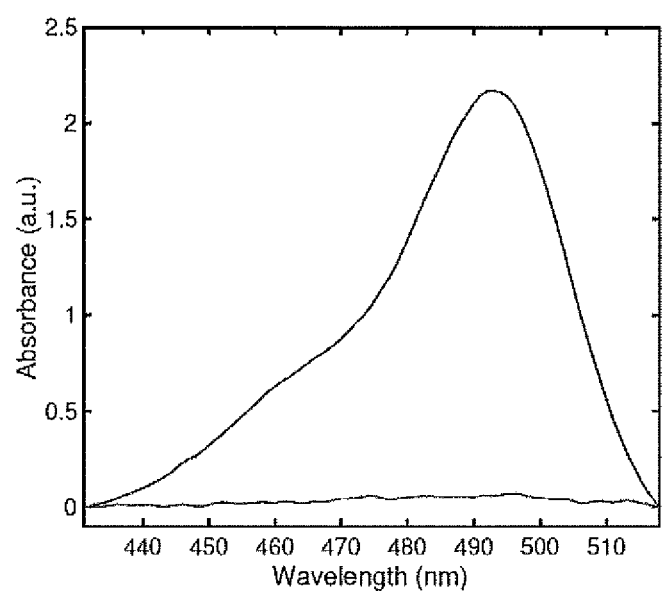
FIG. 11 shows UV-vis absorbance spectra of hybrid liposomes containing 20% DMPC in a solution of 1 mg/ml fluorescein labeled dextran (dark grey), and isolated liposomes (light grey) in an exemplary embodiment of the invention. The first curve contains contributions from free and encapsulated dextran while the second curve shows encapsulated dextran, only.

UV-Visible light spectroscopy: The encapsulation efficiency and the resistance to mechanical stress was determined using UV-visible light spectroscopy using a Nanophotometer from IMGEN. The liposomes were prepared in a 1 mg/ml solution of fluorescein dextran, as described above. The liposomes were then isolated by centrifuging for 60 min at 20,000 g, and refilled to a total volume of 2 ml. UV-visible spectra were taken before and after the centrifugation process. Before centrifugation, the absorbance contains contributions from free dextran in the solution and from dextran encapsulated in liposomes. After centrifugation and liposome isolation, only encapsulated dextran contributes to the signal. The efficiency E is calculated by $$E = \frac{(I_{enc} - I_{pureliposomes})}{I_{enc} + I_{free}} \quad (4)$$

where $I_{enc}$ and $I_{enc+free}$ are the integrated intensities of the characteristic absorbance peak of fluorescein (430-520 nm) for the encapsulated and encapsulated+free dextran molecules, respectively. Corresponding absorbance spectra for hybrid liposomes containing 20% DMPC are shown in FIG. 11. The resistance to mechanical stress was determined by a lysis assay. Liposomes were prepared according to the previously described protocol using phosphate buffer saline containing 1 mg/ml fluorescein labeled dextran. The solution was then centrifuged for 60 min at 20,000 g. The supernatant was removed and replaced by phosphate buffer saline at varying molar concentrations (1 mM-10 mM) increasing the osmotic and mechanical stress. The samples were allowed to rest for 30 min and afterwards centrifuged for additional 60 min at 20,000 g. The degree of lysis was determined by determine the absorbance of the fluorescein peak. A low degree of lysis results in a low concentration of free dextran in the supernatant while increased lysis is indicated by a leveled dextran concentration and thus a higher absorbance.

Statistical analysis: All samples were prepared and measured in replicates and checked for consistency. Errors were determined by the respective experimental errors and consequent error propagation.

While the present invention has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term herein is found to be defined differently in a document incorporated herein by reference, the definition provided herein is to serve as the definition for the term.

BIBLIOGRAPHY

The following references are specifically incorporated herein by reference.

[1] A. Samad, Y. Sultana, M. Aqil, Current drug delivery, 2007, 4, 297.
[2] A. Laouini, C. Jaafar-Maalej, I. Limayem-Blouza, S. Sfar, C. Charcosset, H. Fessi, Journal of colloid Science and Biotechnology, 2012, 1, 147.
[3] B. S. Pattni, V. V. Chupin, V. P. Torchilin, Chemical reviews, 2015, 115, 10938.
[4] L. R. C. Pedrosa, O. van Tellingen, T. Soulli_e, A. L. Seynhaeve, A. M. Eggermont, T. L. ten Hagen, M. Verheij, G. A. Koning, European Journal of Pharmaceutics and Biopharmaceutics, 2015, 94, 207.
[5] T. R. Hoare, D. S. Kohane, Polymer, 2008, 49, 1993.
[6] L. Sercombe, T. Veerati, F. Moheimani, S. Y. Wu, A. K. Sood, S. Hua, Frontiers in pharmacology, 2015, 6, 286.
[7] G. M. Ihler, R. H. Glew, F. W. Schnure, Proceedings of the National Academy of Sciences, 1973, 70, 2663.
[8] V. R. Muzykantov, Expert opinion on drug delivery, 2010, 7, 403.
[9] M. Magnani, American journal of hematology, 2017, 92, 979.
[10] V. Leuzzi, R. Micheli, D. D'Agnano, A. Molinaro, T. Venturi, A. Plebani, A. Soresina, M. Marini, P. F. Leali, I. Quinti, et al., Neurology-Neuroimmunology Neuroinammation, 2015, 2, e98.
[11] S. Zaitsev, D. Spitzer, J.-C. Murciano, B.-S. Ding, S. Tliba, M. A. Kowalska, O. A. Marcos-Contreras, A. Kuo, V. Stepanova, J. P. Atkinson, et al., Blood, 2010, 115, 5241.
[12] S. Zaitsev, M. A. Kowalska, M. Neyman, R. Carnemolla, S. Tliba, B.-S. Ding, A. Stonestrom, D. Spitzer, J. P. Atkinson, M. Poncz, et al., Blood, 2012, 119, 4779.
[13] W. M. Armstead, K. Ganguly, J. W. Kiessling, X.-H. Chen, D. H. Smith, A. A. Higazi, D. B. Cines, K. Bdeir, S. Zaitsev, V. R. Muzykantov, Journal of Cerebral Blood Flow & Metabolism, 2009, 29, 1463.
[14] W. M. Armstead, K. Ganguly, J. Kiessling, J. Riley, X.-H. Chen, D. H. Smith, S. C. Stein, A. A. Higazi, D. B. Cines, K. Bdeir, et al., Journal of neurochemistry, 2010, 113, 303.
[15] K. M. Lorentz, S. Kontos, G. Diaceri, H. Henry, J. A. Hubbell, Science advances, 2015, 1, e1500112.
[16] D. Pan, O. Vargas-Morales, B. Zern, A. C. Anselmo, V. Gupta, M. Zakrewsky, S. Mitragotri, V. Muzykantov, PLoS One, 2016, 11, e0152074.
[17] V. R. Muzykantov, J. C. Murciano, R. P. Taylor, E. N. Atochina, A. Herraez, Analytical biochemistry, 1996, 241, 109.
[18] Y. He, R. Li, H. Li, S. Zhang, W. Dai, Q. Wu, L. Jiang, Z. Zheng, S. Shen, X. Chen, et al., ACS nano, 2019, 13, 4148.
[19] Q. Jiang, Y. Liu, R. Guo, X. Yao, S. Sung, Z. Pang, W. Yang, Biomaterials, 2019, 192, 292.
[20] Y. Liu, X. Wang, B. Ouyang, X. Liu, Y. Du, X. Cai, H. Guo, Z. Pang, W. Yang, S. Shen, Journal of Materials Chemistry B, 2018, 6, 7033.
[21] S. Himbert, R. J. Alsop, M. Rose, L. Hertz, A. Dhaliwal, J. M. Moran-Mirabal, C. P. Verschoor, D. M. E. Bowdish, L. Kaestner, C. Wagner, M. C. Rheinstadter, Scienti_c Reports, 2017, 7, 39661.
[22] R. J. Alsop, R. M. Schober, M. C. Rheinstadter, Soft Matter, 2016, 12, 6737.
[23] M. C. Smith, R. M. Crist, J. D. Clogston, S. E. McNeil, Analytical and bioanalytical chemistry, 2017, 409, 5779.
[24] M. W. Rampling, Biochemical pharmacology, 1976, 25, 751.
[25] D. Flormann, K. Schirra, T. Podgorski, C. Wagner, Rheologica Acta, 2016, 55, 477.

[26] D. Flormann, O. Aouane, L. Kaestner, C. Ruloff, C. Misbah, T. Podgorski, C. Wagner, Scientifc reports, 2017, 7, 7928.
[27] H. I. Ingolfsson, M. N. Melo, F. J. Van Eerden, C. Arnarez, C. A. Lopez, T. A. Wassenaar, X. Periole, A. H. De Vries, D. P. Tieleman, S. J. Marrink, Journal of the american chemical society, 2014, 136, 14554.
[28] D. Lingwood, K. Simons, Science, 2010, 327, 46.
[29] M. C. Rheinstadter, O. G. Mouritsen, Curr. Opin. Colloid Interface Sci., 2013, 18, 440.
[30] C. L. Armstrong, D. Marquardt, H. Dies, N. Ku cerka, Z. Yamani, T. A. Harroun, J. Katsaras, A.-C. Shi, M. C. Rheinstadter, PLOS ONE, 2013, 8, e66162.
[31] L. Toppozini, S. Meinhardt, C. L. Armstrong, Z. Yamani, N. Kucerka, F. Schmid, M. C. Rheinstadter, Physical review letters, 2014, 113, 228101.
[32] J. T. Dodge, G. B. Phillips, Journal of lipid research, 1967, 8, 667.
[33] V. L. Lew, A. Hockaday, C. J. Freeman, R. M. Bookchin, The Journal of cell biology, 1988, 106, 1893.
[34] S. Bhattacharjee, Journal of Controlled Release, 2016, 235, 337.
[35] M. Ribeiro, M. Domingues, J. Freire, N. Santos, M. Castanho, Frontiers in cellular neuroscience, 2012, 6, 44.
[36] T. Nii, F. Ishii, International journal of pharmaceutics, 2005, 298, 198.
[37] A. Zaltzman, C. Van den Berg, V. Muzykantov, B. Morgan, Biochemical Journal, 1995, 307, 651.
[38] V. R. Muzykantov, M. D. Smirnov, A. L. Klibanov, FEBS letters, 1993, 318, 108.
[39] V. R. Muzykantov, M. D. Smirnov, G. P. Samokhin, Biochimica et Biophysica Acta (BBA)-Biomembranes, 1992, 1107, 119.
[40] V. R. Muzykantov, M. D. Smirnov, A. L. Klibanov, Journal of immunological methods, 1993, 158, 183.
[41] C. H. Villa, D. C. Pan, I. H. Johnston, C. F. Greineder, L. R. Walsh, E. D. Hood, D. B. Cines, M. Poncz, D. L. Siegel, V. R. Muzykantov, Blood advances, 2018, 2, 165.
[42] S. L. Veatch, S. L. Keller, Biochimica et Biophysica Acta (BBA)-Molecular Cell Research, 2005, 1746, 172.
[43] J. Juhasz, F. J. Sharom, J. H. Davis, Biochimica et Biophysica Acta (BBA)-Biomembranes, 2009, 1788, 2541.
[44] J. Juhasz, J. H. Davis, F. J. Sharom, Biochemical Journal, 2010, 430, 415.
[45] J. Juhasz, F. J. Sharom, J. H. Davis, Biochimica et Biophysica Acta (BBA)-Biomembranes, 2009, 1788, 2541.
[46] M. J. Skaug, M. L. Longo, R. Faller, The Journal of Physical Chemistry B, 2011, 115, 8500.
[47] N. F. Morales-Penningston, J. Wu, E. R. Farkas, S. L. Goh, T. M. Konyakhina, J. Y. Zheng, W. W. Webb, G. W. Feigenson, Biochimica et Biophysica Acta (BBA)-Biomembranes, 2010, 1798, 1324.
[48] A. Khondker, D. J. Malenfant, A. K. Dhaliwal, M. C. Rheinstadter, ACS infectious diseases, 2018, 4, 926.
[49] J. F. Nagle, M. C. Wiener, Biophys. J., 1989, 55, 309.
[50] S. Jo, T. Kim, V. G. Iyer, W. Im, Journal of computational chemistry, 2008, 29, 1859.
[51] Y. Qi, H. I. Ingolfsson, X. Cheng, J. Lee, S. J. Marrink, W. Im, Journal of chemical theory and computation, 2015, 11, 4486.

What is claimed is:

1. A method of preparing a hybrid biological membrane, the method comprising doping an endogenous bilayer with one or more modifying lipid molecules and drying the hybrid biological membrane on a solid substrate having a lipid bilayer compatible surface, wherein the endogenous bilayer lipids and the modifying lipid molecules anneal to form a substantially homogenous hybrid biological membrane structure.

2. The method of claim 1, further comprising purifying the endogenous bilayer prior to doping and/or removing cellular contents from the endogenous bilayer prior to doping.

3. The method of claim 1, wherein drying the hybrid biological membrane comprises incubating the hybrid biological membrane on the solid substrate at a temperature of from about 0° C. to about 100° C. and a relative humidity of from about 0% to about 100%.

4. The method of claim 3, wherein the solid substrate is hydrophilic.

5. The method of claim 3, the method further comprising incubating the hybrid biological membrane on the solid substrate to increase homogeneity of the hybrid biological membrane.

6. The method of claim 1, further comprising rehydrating the hybrid biological membrane.

* * * * *